(12) United States Patent
Wenzel et al.

(10) Patent No.: US 8,715,263 B2
(45) Date of Patent: *May 6, 2014

(54) INCONTINENCE ARTICLE IN THE FORM OF BRIEFS

(75) Inventors: Benjamin Wenzel, Neu-Ulm (DE); Fridmann Hornung, Santiago (CL)

(73) Assignee: Paul Hartmann AG, Heidenheim (DE)

( * ) Notice: Subject to any disclaimer, the term of this patent is extended or adjusted under 35 U.S.C. 154(b) by 551 days.

This patent is subject to a terminal disclaimer.

(21) Appl. No.: 12/737,411

(22) PCT Filed: Aug. 27, 2009

(86) PCT No.: PCT/EP2009/006204
§ 371 (c)(1),
(2), (4) Date: Jan. 11, 2011

(87) PCT Pub. No.: WO2010/028751
PCT Pub. Date: Mar. 18, 2010

(65) Prior Publication Data
US 2011/0112500 A1    May 12, 2011

(30) Foreign Application Priority Data
Sep. 10, 2008  (DE) .................. 10 2008 046 607

(51) Int. Cl.
*A61F 13/15*    (2006.01)
*A61F 13/20*    (2006.01)

(52) U.S. Cl.
USPC ........... 604/385.31; 604/385.22; 604/385.25; 604/387; 604/394; 604/396

(58) Field of Classification Search
USPC ............ 604/385.01, 385.22–385.27, 385.31, 604/386–387, 394, 396
See application file for complete search history.

(56) References Cited

U.S. PATENT DOCUMENTS

| | | | |
|---|---|---|---|
| 7,014,632 B2 * | 3/2006 | Takino et al. | 604/393 |
| 7,621,900 B2 * | 11/2009 | Van Gompel et al. | 604/385.24 |
| 7,993,320 B2 * | 8/2011 | Hornung et al. | 604/385.3 |
| 8,016,806 B2 * | 9/2011 | Hornung et al. | 604/385.3 |
| 8,025,652 B2 * | 9/2011 | Hornung et al. | 604/385.3 |
| 8,038,662 B2 * | 10/2011 | Hornung et al. | 604/385.3 |
| 8,100,173 B2 * | 1/2012 | Hornung et al. | 165/265 |
| 8,187,269 B2 * | 5/2012 | Shadduck et al. | 606/41 |
| 8,257,331 B2 * | 9/2012 | Fujioka et al. | 604/385.24 |
| 8,267,907 B2 * | 9/2012 | Soroudi | 604/294 |
| 8,444,617 B2 * | 5/2013 | Wennerback | 604/385.01 |
| 2002/0007172 A1 | 1/2002 | Takei | |
| 2002/0049421 A1 | 4/2002 | Hayase | |
| 2002/0173764 A1 | 11/2002 | Takino | |
| 2003/0023219 A1 | 1/2003 | Nakaoka | |
| 2005/0020991 A1 | 1/2005 | Van Gompel | |
| 2008/0114325 A1 | 5/2008 | Edwall | |
| 2012/0046632 A1 * | 2/2012 | Malowaniec | 604/385.24 |

FOREIGN PATENT DOCUMENTS

| | | |
|---|---|---|
| DE | 10 2007 002 290 | 7/2008 |
| EP | 1 415 629 | 5/2004 |
| EP | 1 459 719 | 9/2004 |
| WO | WO 2004/052260 | 6/2004 |

\* cited by examiner

*Primary Examiner* — Michele M Kidwell
(74) *Attorney, Agent, or Firm* — Paul Vincent

(57) ABSTRACT

An incontinence article (2) in the form of briefs has a front stomach portion (4) and a rear back portion (6), which are connected to one another at lateral seam regions (14) on both sides. A crotch portion (8) has an absorption pad (7) and extends in a longitudinal direction (9). A topsheet material (84) or a topsheet (84) and a backsheet material (62) form a transverse overhang (66a,66b) extending outside longitudinal borders (46) of the absorption pad (7). The overhang (66a,66b) has a reinforcing means (200) in a region (204) bridging the respective longitudinal border (46) of the absorption pad (7). The reinforcing means (200) comprises or consists of a reinforcing coating (202 and is disposed on the inner face (85) of the topsheet material (84).

16 Claims, 11 Drawing Sheets

INCONTINENCE ARTICLE IN THE FORM OF BRIEFS

This application is the national stage of PCT/EP2009/006204 filed on Aug. 27, 2009 and claims Paris Convention Priority to DE 10 2008 046 607.7 filed Sep. 10, 2008.

BACKGROUND OF THE INVENTION

The invention concerns an incontinence article in the form of pants for the absorption of body excretions, comprising a front belly portion and a rear back portion, which are connected to one another at lateral seam regions on both sides at the manufacturer's to form a belly and back band which is continuous in the transverse or peripheral hip direction and has a hip opening that is closed in the peripheral hip direction, and comprising a crotch portion, which has an absorbent body and extends in a longitudinal direction between the belly portion and the back portion and is undetachably joined to the belly portion and to the back portion, wherein the crotch portion, the belly portion and also the back portion define the leg openings of the incontinence article. An incontinence article of this type comprising three components is e.g. disclosed in WO 2004/052260 A1. This specific product concept realizes an H-shaped basic structure of the incontinence article after joining the crotch portion that extends in the longitudinal direction to the belly portion that substantially extends in the transverse or peripheral hip direction and to the correspondingly extending back portion in a state in which all three components are flatly spread out. The incontinence article is then modularly formed from the crotch portion, belly portion and back portion components. These components are initially advantageously connected to each other via the crotch portion and the belly portion and the back portion are advantageously subsequently connected at their mutual lateral seam regions. This connection is realized at the manufacturer's to obtain the form of pants. This connection is typically undetachable. The pant shape may, however, also be detachable along a predetermined breaking line which may extend, in particular, in the lateral seam region, e.g. for removing a used incontinence article from a person in need of care.

In principle, incontinence articles in the form of pants differ from incontinence articles in the form of normal diapers that can be conventionally opened and closed in that the hip size is generally predetermined and adjustment to different body sizes is obtained by providing a number of basic sizes and by providing an article that can be elastically stretched. Towards this end, elastification means, in particular in the form of bands or threads, frequently called Lycra threads, are connected in a pre-stretched state (stretch-bond method) to chassis materials of the incontinence article, i.e. they are fixed in a pre-stretched state to the chassis materials e.g. using adhesive. Due to their pretension, these elastification means gather the chassis materials and thereby form folds. The incontinence article or the elasticised chassis materials of the incontinence article can be elastically stretched again when the incontinence article is applied to the user as pants. Incontinence articles in the form of pants comprising chassis materials that are elasticised in this fashion are well known and are e.g. also discussed in the above-mentioned document WO 2004/052260 A1.

For producing the H-shaped basic structure, i.e. for connecting the crotch portion to the belly portion and to the back portion, a joint must be generated between these components which is appropriate for all requirements under normal conditions of use to prevent detachment of the connection between crotch portion and belly portion or back portion under large tensile loads. Large forces are sometimes generated during wear of an incontinence article in the form of pants due to the weight of an absorbent body being loaded with a considerable amount of liquid, and due to transfer of large tensile forces within the chassis materials by the elastification means which are normally joined to the chassis materials in a stretch-bond method and also by tensile forces that are transferred by the movements of the user. It has thereby turned out that this high tensile stress surprisingly occurs both with mobile users who use the incontinence article quasi like an undergarment and also with bedridden persons in need of care whose mobility is highly limited. Due to uncontrolled and, in particular, also slow movements, the chassis materials of the incontinence article are unavoidably subjected to the generated tensile stress. The joints of the incontinence article, i.e. exactly between the crotch portion and the belly portion and between the crotch portion and the back portion are greatly stressed in exactly these situations.

When a large amount of adhesive material is used, which is applied, in particular, in an extensive fashion, for producing a stable connection between the crotch portion and the belly portion and between the crotch portion and the back portion, which connection can be constantly subjected to tension, the overlapping area between the crotch portion and the belly portion or the back portion is disadvantageously stiffened. This is perceived as being unpleasant and can also prevent the desired stretchability of the chassis materials in this area, wherein it must thereby also be mentioned that extensive elasticity is often not desired in this area. This case, however, is also problematic in that the adhesive materials prevent achievement of the desired product properties.

The use of thicker materials, i.e. materials having a high surface density, for the crotch portion for producing a stable connection between the crotch portion and the back portion and between the crotch portion and the belly portion, a connection which can be constantly subjected to tension, also disadvantageously entails extensive stiffening in the overlapping area between the crotch portion and the belly portion or the back portion.

Materials having a small surface density are desired due to the usual associated flexibility and therefore improved adjustability and, in particular, also the softness for the design of the crotch portion. However, flat arrangement of such materials on other components, such as the back portion or the belly portion, is often only possible to a limited degree due to their insufficient natural stability, with the disadvantageous result of less stable connections due to non-planar supporting surfaces, i.e. surfaces which are not free from folds.

Departing therefrom, it is the underlying purpose of the present invention to solve the above-mentioned problems, i.e. in particular, to form a stable connection between the crotch portion and the belly portion and/or between the crotch portion and the back portion of an incontinence article in the form of pants of this type without thereby impairing the wear comfort or consequently further impairing the functionality of the incontinence article.

SUMMARY OF THE INVENTION

This object is achieved in accordance with the invention by an incontinence article comprising the features of the independent article of manufacture claim.

Since the H-shaped basic structure of the incontinence article is modularly formed from the components crotch portion, belly portion and back portion, and since the crotch portion has a projection on both sides of the longitudinal edges of the absorbent body of highly flexible, chassis-forming covering materials having a low surface density, optimum application to the crotch portion is difficult, in particular, when working at high machine speeds, in particular, in an order of magnitude of several 100 m/min, which is normal for the production of modern incontinence articles.

Incontinence articles moreover have contours that support adjustability. The crotch portion or the longitudinal edges of the crotch portion which delimit the leg openings advantageously have a curved contour. The belly portion and the back portion may advantageously have an edge contour extending towards the transverse center axis for defining the leg openings. It is also difficult in terms of production technology to obtain a clear contour for a projection on both sides of the longitudinal edges of the absorbent body of chassis-forming covering materials having a small surface density.

A further object of the present invention consists in providing a method for producing an incontinence article in the form of pants comprising the above-mentioned features, which can be performed in an economical fashion, and takes into account, in particular, the above-mentioned aspects of stable connections between the crotch portion and the belly portion or the back portion, thereby maintaining the wear comfort and the functionality.

This object is achieved by a method for producing an incontinence article of this type comprising the method steps according to the independent method claim.

Advantageous further developments of incontinence articles and methods can be extracted from the respective dependent claims.

The invention has shown that this type of construction of an incontinence article in the form of pants has substantial advantages:

A large overlapping area between the crotch portion and the belly portion and also between the crotch portion and the back portion is realized in that the crotch portion is formed having a very extensive width in the transverse direction of at least 200 mm, and the overall projection of the cover sheet material or the cover sheet and backsheet material in the transverse direction past the respective longitudinal edges of the absorbent body, i.e. on both sides of the longitudinal edges of the absorbent body, amounts to at least 25% with respect to the maximum width of the crotch portion. Due to the large projection of the chassis materials of the crotch portion in the transverse direction past the absorbent body, an overlapping area having a large surface is moreover obtained between the crotch portion and the belly portion or the back portion outside of the absorbent body, which, in turn, has technically functional advantages. The connection between the crotch portion and the belly portion or the back portion must be optimized and the component of the absorbent body should also be minimally influenced. The larger the overlapping area between the crotch portion and the belly portion or the crotch portion and the back portion outside of the absorbent body, the larger the degrees of freedom in view of the design of a functional connection. A large projection of the chassis materials in the transverse direction on both sides of the longitudinal edges of the absorbent body also advantageously creates the possibility of providing additional leg elastification means in the longitudinal direction on both sides of the absorbent body, which extend at a maximum separation from the absorbent body. This advantageously prevents the absorbent body from being subjected to tensile and compressive forces by the leg elastification means, i.e. forces that would twist the absorbent body. These incalculable forces have a negative effect on the absorption behavior of the absorbent body. This could lead to uncontrollable compression or widening of absorbent body areas, which influence the intended absorptive behavior in a disadvantageous fashion. In this connection, the relatively large overlapping area between the crotch portion and the belly portion or between the crotch portion and the back portion is also characterized in that the crotch portion overlaps at least 12% of the surface of the belly portion in the front overlapping area and at least 20% of the surface of the back portion in the rear overlapping area.

The crotch portion is formed by a backsheet material or a cover sheet material having a small surface density, i.e. 10 to 40 g/m$^2$ or 5 to 20 g/m$^2$, thereby ensuring the desired softness, adjustability and drapeability in these sensitive body regions for the user of the incontinence article.

The small surface density and the associated smaller natural stability increase the danger that the chassis materials are torn. On the other hand, chassis materials having a small surface density and a relatively large projection are also disadvantageous in that the projection tends to form undesired folds, i.e. local material accumulations both in the transverse and/or longitudinal directions due to the small natural stability. The disadvantage thereby consists in that the folds in the projection reduce the stability of the connection to the belly portion and/or to the back portion.

Additional but uncoordinated folds of the chassis-forming covering materials of the crotch portion are disadvantageous in view of optimum connection and also in that the belly portion and the back portion have second elastification means in the area on the crotch side facing the leg openings. The elastification means enable stretchability and adjustment to different body sizes and shapes as desired.

It has turned out that, in accordance with the invention, the areas in the front and/or rear overlapping areas, which are problematic due to the low surface density of the chassis materials of the crotch portion, can be stabilized by a reinforcing means in the respective projection on both sides of the longitudinal edges of the absorbent body. The reinforcing means is thereby provided in one area bridging the respective longitudinal edge of the absorbent body. The reinforcing means thereby advantageously covers each longitudinal edge area of the absorbent body and then merges via the longitudinal edge of the absorbent body into the adjoining subregion of the projection. Due to its surface density, the absorbent body itself has a larger natural stability than the chassis-forming covering materials of the crotch portion. By arranging the reinforcing means in the longitudinal edge area of the absorbent body, the natural stability of the absorbent body is effectively transferred by means of the reinforcing means to the respectively bordering subregion of the projection and then continued through the reinforcing means as such. Starting from the longitudinal edge area via the longitudinal edge of the absorbent body to the bordering subregion of the projection and finally to the longitudinal edge of the crotch portion, a type of overall "reinforcing profile" with decreasing strength is thereby advantageously generated. The reinforcing means is only provided in a subregion of the projection, i.e. this subregion has a smaller width than the projection, i.e. terminates upstream of the longitudinal edges of the crotch portion, thereby preventing hardening of these edge areas. Hardened edge areas would irritate the skin of the user and thereby reduce the wear comfort of the incontinence article. The formation of the reinforcing means in a subregion of the projection is moreover also advantageous in that, depending on the embodiment of the reinforcing means, in particular, in the form of an adhesive, production-related undesired leakage of the reinforcing means out of the chassis-forming covering materials is prevented.

The reinforcing means in the form of a reinforcing coating also maintains the desired adjustability of the incontinence article in these areas. It was discovered that the use of coatings of a surface density of 1 to 30 g/m² is advantageous in order to obtain a sufficiently large stability in combination with the chassis materials without thereby causing unnecessary stiffening.

The arrangement of the reinforcing means on the inner side of the cover sheet material, i.e. on the upper side facing away from the user and thereby on the upper side of the cover sheet material facing the absorbent body, is advantageous since the skin-friendly properties of the non-woven structure of the cover sheet material are maintained for the user. Since the reinforcing means has a smaller extension in the subregion of the projection compared to the projection in the transverse direction, the cover sheet material is used as a type of protective sleeve for the reinforcing means. Otherwise, when arranged on the outer side, i.e. on the upper side of the cover sheet material facing the user, it could cause discomfort for the user due to the nature of the reinforcing means, or further additional measures would have to be taken to ensure a skin-friendly surface of the reinforcing means. Arrangement of the reinforcing means formed in the subregion of the projection in the transverse direction and having a smaller extension than the projection on the outer side of the cover sheet material would cause further disadvantages in that frictional forces caused by movement of the user could result in partial detachment of the reinforcing means.

The projection in the subregion, which is covered by the reinforcing means, in the front and/or rear overlapping region may advantageously be arranged largely without folds on the belly portion and/or the back portion. "Largely without folds" thereby means that the material layers themselves that form the projection and also in relation to the bordering material layers of the components to be connected thereto largely do not show any local material displacement and material accumulations but that the material layers are largely flush joined as viewed in the flatly extended and flatly spread-out state. This largely fold-free arrangement is also advantageous in that the restoring forces and folds deliberately introduced by the first and/or second elastification means in the corresponding areas are not disadvantageously influenced by the otherwise undesired local material accumulations of the projection.

A "projection" thereby means the extension of the cover sheet material or the cover sheet material and of the backsheet material laterally past the longitudinal edges of the absorbent body, wherein the maximum extension, i.e. the outermost extent of the cover sheet material and/or the backsheet material located at a maximum distal separation from the longitudinal edges of the absorbent body is used. The backsheet material and/or the cover sheet material may advantageously consist of several components, e.g. the cover sheet material may advantageously be a composite of a topsheet material and of barrier means that border on both sides in the longitudinal direction. This means that also for composites, i.e. composite cover sheet materials and/or backsheet materials, the respective maximum, i.e. the outermost distal outer extension of the composite, is used when considering the projection.

The backsheet material and the cover sheet material advantageously have the same transverse extension. They are congruent, i.e. coincide.

It is also advantageous for the backsheet material and the cover sheet material not to be congruent with one another. The backsheet material preferentially has a smaller transverse extension than the cover sheet material. The backsheet material that could possibly disturb the user in view of wear comfort, such as e.g. a foil, is thereby covered by the skin-friendly non-woven material of the cover sheet material.

The "inner side" of the cover sheet material, the topsheet material, the backsheet material or the barrier means is the upper side of the respective material facing the absorbent body.

The features of the independent article of manufacture claim create an overall incontinence article in the form of pants having the above-mentioned three-component design, which realizes a safe connection of the components without thereby impairing the wear comfort or the functionality of the incontinence article or its components.

In a further advantageous development of the invention, only the projection has reinforcing means in the rear overlapping area. In particular, for persons with little mobility, i.e. also bedridden persons, the rear overlapping area is particularly stressed due to the fact that the person is mainly lying on his/her rear side. Undesired folds which could disadvantageously also cause skin irritations, in particular, in the rear overlapping area, are advantageously avoided through introduction of reinforcing means.

In another advantageous further development, the reinforcing means is mounted both in the front and also in the rear overlapping area in each case in an area bridging the respective longitudinal edge of the absorbent body. This provides an incontinence article which is independent of its subsequent field of use and can therefore be universally used, and meets different requirement profiles.

This is based on the understanding that the reinforcing means provided in the front and/or rear overlapping areas on both sides of the absorbent body in the longitudinal direction are each preferably disposed symmetrically with respect to one another and preferably also have the same design, i.e. coincide with respect to their longitudinal extension, width, overlapping degree, material composition and/or surface density.

In dependence on the field of use of the incontinence article and also on the mobility of the user, it may be advantageous to provide the reinforcing means in the front and in the rear overlapping areas with different designs. The reinforcing means advantageously differ in the front and rear overlapping areas at least with respect to one of the parameters longitudinal extension, width, overlapping degree, material composition and/or surface density and/or combinations thereof.

In a further advantageous embodiment of the invention, the reinforcing means extends in the longitudinal direction at least to the transverse edge of the absorbent body and to the transverse edge of the belly portion and/or back portion facing the crotch. Due to this extension of the reinforcing means in the longitudinal direction between the respective transverse edge of the absorbent body and the respective transverse edge of the belly portion or back portion facing the crotch, at least the areas along the absorbent body are reinforced and stabilized. These areas would otherwise be exposed to a less stable connection with the components of the belly portion and/or the back portion due to uncontrolled folds of the projection.

In dependence on the field of use of the incontinence article and the mobility of the user, it may be advantageous to vary the length of the reinforcing means in the front and rear overlapping areas. The reinforcing means also advantageously has a greater longitudinal extension in the rear overlapping area than in the front overlapping area.

The reinforcing means preferentially extends in the longitudinal direction at least to the respective transverse edge of the absorbent body and to the transverse edge, facing the crotch, both of the belly portion and of the back portion.

In a further preferred embodiment, the reinforcing means extends in the direction towards the transverse center axis starting from the front and/or rear overlapping area via the respective transverse edge of the belly portion and/or back portion, which faces the crotch.

In one further particularly preferred embodiment, the reinforcing means in the front overlapping area and the reinforcing means in the rear overlapping area extend towards the transverse center axis and are joined.

In the subregion covered by the reinforcing means, the reinforcing means advantageously has a width G' in the transverse direction of the projection of more than 5 mm, preferably more than 10 mm, but preferably less than 50 mm, preferably less than 40 mm, moreover preferably less than 30 mm.

In a further advantageous fashion, the ratio G'/H between the subregion, covered by the reinforcing means, of the respective projection with a width G' and the respective projection with a width H is at least 0.10, in particular at least 0.15, moreover in particular at least 0.20, but preferably maximally 0.80, in particular maximally 0.75, moreover, in particular, maximally 0.70. This reinforcing means ratio in the respective projection provides sufficient reinforcement of the chassis-forming covering materials of the crotch portion, thereby avoiding excessive use of additional material and associated costs.

Furthermore, the reinforcing means advantageously covers the longitudinal edge area of the absorbent body in the transverse direction in each case with a width G" of more than 5 mm, preferably more than 10 mm, but advantageously less than 50 mm, preferably less than 40 mm, moreover preferably less than 30 mm.

The ratio G"/H between the respective longitudinal edge area covered by the reinforcing means with a width G" and the respective projection with a width H is at least 0.10, in particular at least 0.15, moreover, in particular, at least 0.20, but preferably maximally 0.80, in particular, maximally 0.75 and moreover maximally 0.70.

With particular preference, the reinforcing means covers the longitudinal edge area of the absorbent body in the transverse direction in total, i.e. on both sides, with a ratio of at least 5%, in particular at least 10%, moreover in particular at least 15% and at most 35%, in particular at most 30%, moreover in particular at most 25% with respect to the width K of the absorbent body.

The ratio G"/K between the respective longitudinal edge area covered by the reinforcing means with width G" and the absorbent body with a width K is at least 0.02, in particular at least 0.04, moreover, in particular, at least 0.06, but preferably at most 0.30, in particular at most 0.25 and moreover, in particular, at most 0.20.

The overlapping between the reinforcing means and the absorbent body which exists substantially only in the longitudinal edge area impairs the surface provided by the absorbent body for receiving liquids only to a small degree. However, this small overlapping ratio between the reinforcing means and the absorbent body yields a sufficiently large area for obtaining a certain transfer of natural stability of the absorbent body onto the combination of reinforcing means and chassis-forming covering materials of the crotch portion.

With particular preference, the reinforcing means has an overall width G of 10 to 60 mm, in particular 15 to 55 mm, moreover, in particular 20 to 50 mm, moreover, in particular 20 to 40 mm.

In a further advantageous fashion, the reinforcing means is disposed parallel with respect to the longitudinal direction and in the form of a strip having a constant width. In this fashion, the reinforcing means can be introduced into the incontinence article with little technical expense and for this reason more rapidly and at reduced cost.

The reinforcing means in the form of a coating has turned out to be advantageous, since, in dependence on the material, the coating can also penetrate at least partially into the pores of the non-woven cover sheet material or can surround fiber surfaces, thereby producing an advantageous bonding force with the chassis-forming covering materials of the crotch portion.

The reinforcing coatings are advantageously selected from the group of non-adhesive or adhesive coatings. In one particularly advantageous further development of the invention, the reinforcing coating comprises an adhesive, in particular a hot-melt adhesive.

The following adhesives may e.g. be advantageously used as adhesive: D9105ZP or LC3001ZP (H.B. Fuller Deutschland GmbH, An der Roten Bleiche 2-3, 21335 Lüneburg, Germany); H20028 or H2481 (Bostik Nederland B.V., Zeggeveld 10, 4705 RP Roosendaal, The Netherlands); Technomelt Q2415 or Technomelt Q5430 (Henkel KGaA, 40191 Düsseldorf, Germany).

In particular, adhesives are used which can be applied in a contact-free application method. The hot-melt adhesive LC3001ZP from the company Fuller (H.B. Fuller Deutschland GmbH, An der Roten Bleiche 2-3, 21335 Lüneburg, Germany) may be preferentially used.

The adhesive or hot-melt adhesive is moreover, in particular, hydrophobic. This is advantageous in that, in addition to the reinforcing function, a liquid barrier is formed at the same time.

The use of adhesive is advantageously also suited for enhancing the adhesive action of the joining means which connect the backsheet material and/or the cover sheet material and/or the absorbent bodies to each other. The backsheet material and the cover sheet material are advantageously directly connected in the area of the projection by separate joining means such as adhesive, calender welding or ultrasonic welding, in particular up to the longitudinal edge of the crotch portion. Separate joining means of this type are also advantageously provided between the backsheet material and the absorbent body and/or between the cover sheet material and the absorbent body. These joining means are advantageously not provided on the overall surface but in the form of a discontinuous pattern. The adhesive provided for this type of separate joining means may be arranged e.g. in strips, in the form of a grid or in the form of a spiral pattern.

It has also turned out to be advantageous to use the reinforcing coating with a surface density of, in particular, 2 to 20 g/m$^2$, moreover in particular 2 to 10 g/m$^2$.

The reinforcing coating is advantageously applied to the overall surface.

In one further advantageous design, the cover sheet material is a composite of a liquid-permeable topsheet material with longitudinal edges and bordering longitudinal edge areas and with hydrophobic barrier means joined in seams on both sides on the longitudinal edges or longitudinal edge areas of the topsheet material. This composite provides the different requirement profiles in different areas of an incontinence article, i.e. liquid absorption in the center area and retardation of lateral liquid leakage at the edge areas.

In one further embodiment, the hydrophobic barrier means extends past the longitudinal edges of the topsheet material thereby forming an upright barrier means which extends on each of the two sides of the absorbent body in the longitudinal direction and is typically called cuff element or collar element. The distal ends of the barrier means are advantageously provided with elastification means. The barrier means are thereby lifted against the skin surface of the user during use of the incontinence article.

The material webs of the cover sheet material composite may advantageously be fixed to the joints using adhesive, in particular hot-melt adhesive, thermal calendering (thermal bonding) or ultrasonic welding. Fixing may be effected in the form of continuous joints in order to obtain a high bonding force between the topsheet material and the barrier means. A continuous line is thereby feasible. Fixing by intermittently arranged joints, i.e. a sequence of discrete bonding points or bonding lines or any other bonding pattern is also feasible and advantageous.

In one particularly preferred embodiment, the reinforcing means covers the joints of the cover sheet material. The areas which are produced by the joints in the cover sheet material and are possibly problematic, i.e. are subjected to the danger of being torn or be exposed to leaking liquid, are thereby advantageously also reinforced and stabilized in a synergistic fashion by the reinforcing means.

It is moreover advantageous for the projection of the backsheet material and/or the cover sheet material to amount in the transverse direction in total, i.e. on both sides of the longitudinal edges of the absorbent body, to 25 to 50%, in particular 30 to 45% and moreover, in particular, 35 to 45% with respect to the maximum width E of the crotch portion.

In an advantageous further development of the invention, the portion of the surface of the crotch portion with respect to the overall surface of the incontinence article is 25 to 55%, in particular 30 to 47%, moreover, in particular 35 to 47% and moreover, in particular 35 to 45%.

In a further development of the invention, the overlapping area between the crotch portion and the belly portion is designed in such a fashion that the crotch portion overlaps 15 to 40%, in particular 15 to 35% and moreover, in particular 15 to 25% of the surface of the belly portion. The crotch portion advantageously overlaps the belly portion with a surface of 25,000 to 45,000 mm$^2$.

In a further development of the invention, the overlapping area of the crotch portion and the back portion is designed in such a fashion that the crotch portion overlaps 20 to 40%, in particular 20 to 35% and moreover, in particular 22 to 32% of the surface of the back portion. The crotch portion advantageously overlaps the back portion with a surface of 35,000 to 65,000, in particular of 40,000 to 55,000 mm$^2$.

The overlapping of the crotch portion and the back portion is advantageously larger than the overlapping of the crotch portion and the belly portion.

In a particularly advantageous fashion, the crotch portion can be connected to the belly portion and/or the back portion through discontinuous application of adhesive. It has turned out that, when the adhesive is not applied to the overall surface, the properties of the chassis materials are only slightly influenced compared to application of adhesive onto the overall surface for forming the connection between the crotch portion and the belly portion or between the crotch portion and the back portion. When the adhesive is not applied to the overall surface, it may be applied e.g. in the form of a striped pattern, a web-shaped continuous or non-continuous grid structure or island-shaped areas, or in the form of a striped or spirally arranged adhesive structure.

In an advantageous inventive design of the incontinence article, the absorbent body also overlaps 5 to 20%, in particular 5 to 15% of the surface of the belly portion and/or 10 to 20%, in particular 10 to 15% of the surface of the back portion.

The extension of the belly portion and of the back portion in the side seam area in the longitudinal direction is advantageously at least 100 mm, in particular at least 150 mm and, in particular 150 to 220 mm.

The minimum separation between the belly portion and the back portion in the longitudinal direction is advantageously 250 to 400 mm.

The maximum extension of the crotch portion in the transverse direction, i.e. the maximum width is advantageously 200 to 350 mm, in particular 250 to 320 mm.

The relatively large projection of the backsheet material and/or the cover sheet material on both sides of the absorption body therefore means a wide crotch portion with a relatively small absorbent body. For this reason, the crotch portion may be provided with leg elastification means which extend along the leg openings and have a relatively large separation from the absorbent body which comprises a large amount of material and is therefore rigid. This results, in turn, in good sealability and adjustability of the leg opening edges of the crotch portion on both sides. In this case, the absorbent body, which has a large amount of material and being torsion-resistant in contrast to the thin chassis materials, only minimally impairs the formation of a liquid-tight leg end. A liquid-tight leg end can be produced without extremely high tension, which again has a positive effect on the wear comfort of the incontinence article.

In one further particularly advantageous design of the invention, the leg elastification means terminate in the longitudinal direction at least 10 mm, in particular at least 20 mm upstream of the second elastification means. The leg elastification means preferentially terminate in the longitudinal direction before the belly portion and/or before the back portion. The tension and the restoring force thereby exerted do not influence the tension of the second elastification means. Unaffected remain, in particular, the tension within the area of the belly portion and the back portion on the crotch side facing the leg openings, in which area the fanning-out second elastification means are provided.

In a further advantageous fashion, the leg elastification means follow the contour of the absorbent body.

It is also advantageous for the leg elastification means to extend at a varying separation from the absorbent body and to have a larger separation from the absorbent body at their longitudinal ends than at their center.

Thread or band-shaped elastification means, such a rubber or polyether polyurethane or polyester polyurethane threads, preferably elastic threads such as Lycra®, Creora® or Spandex® threads are advantageously used as leg elastification means. The leg elastification means advantageously have a thickness of 300 to 1500 dtex, in particular of 500 to 1200 dtex, moreover in particular of 500 to 900 dtex.

The leg elastification means are advantageously fixed at a pretension of 1.5 to 6.0, in particular of 2.5 to 4.5 to the chassis-forming covering materials of the crotch portion.

The pretension is defined as a factor of the degree of expansion with respect to the non-expanded/relaxed state of the elastification means.

In the further development of the invention as part of the development of incontinence articles in the form of pants, it was discovered that a maximum part of the incontinence article should be designed to be elastically resilient, i.e. stretchable in accordance with the body shape of the user. This resulted in the assumption, which is not always true, that the major part of the cover-forming chassis materials of the incontinence article must be designed with elastically stretchable or elasticised materials, in particular by introducing the above-mentioned elastification means in the stretch-bond method. Irrespective thereof or in addition thereto, one tried to elasticise the leg openings of the incontinence article, if possible, in a continuous fashion in order to obtain reliable side leakage protection.

However, it was not realized that the elastic design of chassis materials also entails substantial disadvantages, in particular by introducing linearly extending elastification means. An extensive elastification of chassis materials, i.e. elastification that is substantially completely continuous, leads to an incontinence article in the form of pants which can, in general, be adjusted to a certain extent to different body shapes, i.e. the article can, in general, be positioned on a user in accordance with its intended use. This, however, is often accompanied by the generation of very strong tensile stress in the chassis materials, which has an unpleasant effect on the user. The elastification means thereby often cut the skin surface of the user, which is perceived as unpleasant and can even cause pain, skin irritations and, in particular, in connection with a moist climate, even skin injuries. Chassis materials that are subjected to a high elongation stress often lie tightly against the skin surface of the user, which generates a moist microclimate in the region of the skin surface even when breathable materials are used, which can also have severe consequences for the skin surface of the user. In this case, instead of a gas phase, a liquid phase forms directly next to the skin surface. Irrespective thereof, great tension in the area of the elastification means produces a great amount of frills, i.e. a large number of folds or crimps per centimeter (as viewed in the direction of the elastic action of the elastification means). This three-dimensional wavy structure is then pressed against the skin surface with great strain exerted by the elastification means, and causes relative motions, in particular, when the user is highly mobile, which again irritate the skin surface and cause unpleasant or even medically problematic skin irritations.

Whenever elastification means are guided in a curved shape or transverse direction with respect to a machine direction, which is often done to obtain extensive elastification of substantially all chassis materials, there is the problem that, due to the component transverse to the machine direction, a larger path must be covered, thereby increasing the pretension of the elastification means in the course of the stretch-bond method. This typically results in a stronger elastic strain resistance of the corresponding chassis areas compared to areas where the elastification means are introduced to extend in the machine direction, which can, in turn, cause severe problems.

In accordance with a further inventive idea, the first elastification means that each extend at a separation from each other and parallel to each other in the transverse and peripheral hip direction are provided for extensive elastification of the belly portion and the back portion. They preferably have the same pretension and are substantially used for extensive continuous and uniform elastification of the belly portion and of the back portion in the area clearly above the leg openings. It is, however, possible for the first elastification means to have a stronger pretension in an upper hip edge area or to provide several of these elastification means at a smaller separation from each other in order to realize a slightly stronger elastification at the hip edge.

It has also turned out i.a. that the tension ratios in the above-mentioned area of the belly portion and of the back portion on the crotch side facing the leg openings are responsible for the above-mentioned problems and can advantageously be designed such that the above-mentioned problems are eliminated or minimized. The area on the crotch side facing the leg openings, in which the second elastification means fan out towards the longitudinal center axis, is advantageously designed in such a fashion that the restoring force generated upon extensive stretching of this area is smaller compared to extensive stretching in an area on the hip side in which only the first elastification means are provided. The term "area on the hip side" defines an area located in the longitudinal direction outside of the area on the crotch side facing the leg openings with the fanning out second elastification means. The restoring force is the force exerted by the belly portion and the back portion against extensive stretching in the direction of extension of the elastification means. In a further development of the invention, it has turned out to be essential that the area on the crotch side facing the leg openings is advantageously designed to have a smaller restoring force upon extensive stretching along the second elastification means compared to bordering areas in the longitudinal direction, which are further away from the crotch and the leg openings, for example, in particular, areas in which the first elastification means are arranged. This improves the wear comfort of the incontinence article and the above-mentioned problems are reduced, since the incontinence article can be stretched to an even greater extent in the crotch area or in the area of the leg openings in correspondence with the body shape without thereby unpleasantly increasing the restoring forces causing the above-mentioned consequences.

In order to determine the restoring forces, the areas of the chassis to be measured may be directly and rigidly clamped in a quasi non-destructive fashion between two clamping jaws of defined identical clamping jaw width, and the restoring forces can be determined under defined stretching, which simulates the state of use, of the areas to be measured by, in particular, 30% or 50% or 80% of the initial length (of the clamping jaw separation when fixing the area to be measured in the unclamped state). The clamping jaws should fix as many elastification means as possible, however, at least two adjacent elastification means, of the area to be measured, and should be oriented substantially perpendicularly with respect to the extension of the elastification means such that stretching between the clamps is performed substantially in the direction of extension of the elastification means.

In a further design of the present invention, it has also turned out that the tension ratios in the above-mentioned area of the belly portion and the back portion on the crotch side facing the leg openings are essential with respect to the wear comfort and can be designed to improve the wear comfort.

The second elastification means advantageously extend starting from the two side seam areas towards a longitudinal center axis of the incontinence article and thereby extend in a curved shape, fanning out with increasing separation from each other.

Towards this end, the area on the crotch side facing the leg openings, in which the second elastification means fan out towards the longitudinal center axis, is designed such that, when this area is extensively stretched, the resulting restoring force decreases towards this crotch portion.

Considering this area of the belly portion and of the back portion on the crotch side facing the leg openings in a direction starting from the respective side seam area towards the crotch portion, i.e. towards a longitudinal center axis of the incontinence article and substantially towards the curved fanning-out of the second elastification means, the restoring force generated by extensive stretching is reduced in this direction. This is the force that is exerted by the belly portion and the back portion in response to extensive stretching. A reduction in this restoring force, which is naturally transferred to the user, considerably improves the wear comfort of the incontinence article.

It has turned out to be particularly advantageous for the restoring force to decrease in the above-mentioned area of the belly portion and of the back portion on the crotch side facing the leg openings in such a fashion that the number of folds per cm in the transverse direction of the incontinence article is decreased towards the crotch portion. In this case, the belly portion and the back portion may be stretched in correspondence with the body shape of the user thereby preventing the generated elastic forces from gathering the chassis material and producing a plurality of folds. As previously explained, a decreasing restoring force in the direction towards the crotch portion means that the force that is generated by extensive stretching decreases with decreasing separation from the crotch portion. The restoring force due to extensive stretching is therefore larger in an area closer to the side seam than in an area closer to the crotch portion.

The above-mentioned tension ratios can be obtained in the most different ways, e.g. by using materials having a different elasticity in the transverse direction in the area on the crotch side facing the leg openings which area also comprises the second elastification means. It would also be feasible to reduce the pretension of the second elastification means with decreasing separation from the crotch portion, i.e. from the outside to the inside in the direction towards a longitudinal center axis. It would moreover also be feasible to reduce the restoring force upon extensive stretching by increasing the separation between the second elastification means, whereby it must then be taken care that this is not compensated for by a strong increase in pretension due to the fan-shaped extension of the elastification means or is even exceeded in the direction of increasing restoring force.

A minimum separation between the second elastification means (separation between directly neighboring elastification means) in the side seam areas of 3 to 8 mm, in particular 3 to 7 m, and moreover, in particular 3 to 6 mm, has turned out to be particularly advantageous.

A maximum separation between the second elastification means (separation between directly neighboring elastification means) on an absorbent body edge or on a longitudinal edge of the crotch portion of 7 to 35 mm, in particular 10 to 32 mm, and moreover, in particular 12 to 30 mm, has also turned out to be advantageous.

It has also turned out to be advantageous for the second elastification means to have a fanning-out degree F $$F=(A-B)/B*100\%$$

of 50 to 900%, in particular 100 to 700% and moreover, in particular, 150 to 550%.

The fanning-out degree F is thereby defined as the ratio between the increasing separation (A−B) and the minimum separation (B) in percent. The values A and B are thereby defined as the separation of the outermost second elastification means in the longitudinal direction from the innermost second elastification means in the longitudinal direction (i.e. not the separation of directly neighboring second elastification means): i.e. A as the maximum separation, in particular, on the longitudinal edge of the crotch portion or absorbent body edge, and B as the minimum separation, in particular, in the side seam area. It was also found out that the fanning-out degree F of the second elastification means is advantageously larger in the back portion than in the belly portion.

Due to the natural body shapes in the back portion or belly portion of a user, the problems mentioned herein are typically more severe in the back or bottom area. For this reason, the maximum separation between the second elastification means on an absorbent body edge in the back portion is advantageously larger than in the belly portion.

It would also be feasible for the second elastification means to continuously extend from one side seam area to the other side seam area, which simplifies, in particular, introduction into a continuous production method compared to a "cut-and-place" process. Due to the overlapping of the crotch portion and the belly portion and the back portion, the absorbent body having a great deal of material may also overlap or cover the belly portion and/or the back portion depending on the design, and thereby also overlap the area of the belly portion and of the back portion on the crotch side facing the leg openings, in which the second elastification means extend. The absorbent body having a great deal of material thereby normally impairs elastic stretchability of the chassis materials. It is moreover not really advantageous for the absorbent body which has a great deal of material to be loaded with additional tension forces. For this reason, it may be advantageous to deactivate the elastic properties of the second elastification means in an overlapping area with the absorbent body of the crotch portion. This deactivation may e.g. be realized by a number of separating cuts through the second elastification means in the overlapping area with the absorbent body, wherein other separating methods such as e.g. using ultrasonic welding or laser are also feasible.

It must also be mentioned that the elastic properties of the first elastification means may also be deactivated in the overlapping area with the absorbent body.

It was mentioned above that, irrespective of the preferential tension ratios, the second elastification means may be subjected to stronger stretching and thereby higher pretension in correspondence of the path of their fanned-out extension during production of the incontinence article compared to an area that is not fanned out, in which they extend substantially at an equal distance from each other in the machine direction. This stronger pretension may be a typical result of introduction of the second elastification means in a conventional stretch-bond method which is therefore not described in detail.

With respect to the overall dimensions of the incontinence article, it has turned out to be advantageous for the separation (C) between the innermost second elastification means, facing the crotch, of the belly portion, and the corresponding innermost second elastification means, facing the crotch, of the back portion to be between 250 and 420 mm.

The separation between the innermost second elastification means facing the crotch and the edge contour, delimiting the leg openings, of the area of the belly portion and back portion facing the leg openings is advantageously 2 to 40 mm, moreover advantageously 3 to 30 mm, in particular advantageously 4 to 15 mm.

Thread-shaped or band-shaped elastification means, such as rubber or polyether polyurethane or polyester polyurethane threads, preferably elastic threads such as Lycra®, Creora® or Spandex® threads, are advantageously used as the first and/or second elastification means.

The first and/or second elastification means preferably have a thickness of 300 to 1500 dtex, in particular 500 to 900 dtex, moreover, in particular 500 to 600 dtex.

The first and/or second elastification means are advantageously fixed to the chassis-forming covering materials of the belly portion and the back portion with a pretension of 1.5 to 6.0, in particular of 2.5 to 5.0. The pretension is thereby defined as the ratio between the degree of stretching compared to the non-stretched/relaxed state of the elastification means.

Irrespective thereof it turned out to be advantageous for the belly portion and the back portion to be substantially continuously extensively transversely elasticised across the longitudinal direction at least outside of the absorbent body, wherein in this case, the advantageous tension relationships must also be maintained or realized.

The chassis-forming materials of the belly portion and/or the back portion advantageously comprise non-woven materials such as spunbonded non-woven materials (S), meltblown non-woven materials (M), SM non-woven materials, SMS non-woven materials, SMMS non-woven materials, card web non-woven materials or Through Air bonded card web non-woven materials. The chassis-forming material of the belly portion and/or the back portion preferentially comprises a spunbonded non-woven material. The non-woven materials used for the belly portion and/or the back portion advantageously have a surface density of 10 to 30 g/m$^2$, moreover preferably of 15 to 25 g/m$^2$. The belly portion and the back portion preferentially comprise a spunbonded non-woven material of polypropylene, in particular, having a surface density of 15 to 25 g/m$^2$.

The chassis-forming covering materials of the crotch portion are advantageously designed as follows:

The backsheet comprises, in particular, a foil, in particular, of a surface density of 10 to 40 g/m$^2$.

The backsheet comprises, in particular, a foil which is liquid-tight and at the same time breathable during use, i.e. a water vapor permeable, in particular microporous foil. The water vapor permeability of the backsheet is, in particular, at least 300 g/m$^2$/24 h, moreover, in particular, at least 1000 g/m$^2$/24 h, moreover, in particular, at least 2000 g/m$^2$/24 h, moreover, in particular, at least 3000 g/m$^2$/24 h, in particular, at least 4000 g/m$^2$/24 h, and moreover, in particular, at most 6000 g/m$^2$/24 h measured in accordance with DIN 53 122-1 (issued 2001-08).

The foil may advantageously be provided with a non-woven coating, which may provide the outer side of the incontinence article facing away from the body with a textile impression. The non-woven coating advantageously consists of a non-woven material, in particular, a spunbonded non-woven material of polypropylene, in particular, having a surface density of 7 to 25 g/m$^2$, 10 to 20 g/m$^2$, in particular 12 to 17 g/m$^2$.

The cover sheet material advantageously comprises non-woven materials such as spunbonded non-woven materials (S), meltblown non-woven materials (M), SM non-woven materials, SMS non-woven materials, SMMS non-woven materials, card web non-woven materials or Through Air bonded card web non-woven materials.

The cover sheet material may thereby be advantageously only formed from topsheet material. The cover sheet material may furthermore advantageously be a composite of topsheet material and barrier means.

In correspondence with the functionality, the following advantageous materials are used.

The topsheet material advantageously comprises non-woven materials, such as spunbonded non-woven materials, card web non-woven materials or Through Air bonded card web non-woven materials. With particular preference, the topsheet material comprises spunbonded non-woven material. The non-woven materials used for the topsheet moreover advantageously have a surface density of 5 to 20 g/m$^2$, 8 to 20 g/m$^2$, moreover preferably 10 to 18 g/m$^2$, in particular advantageously 12 to 16 g/m$^2$. The topsheet preferentially has a hydrophilized spunbonded non-woven material, in particular, of polypropylene, in particular, having a surface density of 12 to 16 g/m$^2$.

The barrier means material advantageously comprises non-woven materials, such as spunbonded non-woven materials, meltblown non-woven materials, card web non-woven materials or Through Air bonded card web non-woven materials. With particular preference, the barrier means material comprises laminates of one or more spunbonded non-woven materials (S) and/or meltblown (M) non-woven layers, in particular SMS laminates or SMMS laminates, in particular, on the basis of polyolefines, such as e.g. polyethelene or polypropylene. Materials of this type are inexpensive and, due to their inherent hydrophobic property, they have a liquid retarding effect.

The non-woven materials used for the barrier means moreover advantageously have a surface density of 5 to 20 g/m$^2$, advantageously 8 to 20 g/m$^2$, moreover advantageously 10 to 18 g/m$^2$. The barrier means preferentially comprises a laminate of spunbonded non-woven and meltblown non-woven layers, in particular of polypropylene, in particular having a surface density of 10 to 18 g/m$^2$.

The absorbent body comprises materials that absorb body fluids such as natural or synthetic fibers, in particular, cellulose fibers, preferably in the form of cellulose fluff. The absorbent core advantageously also comprises super absorbent materials (SAP), in particular, on the basis of surface-linked partially neutralized polyacrylates.

The crotch portion or the longitudinal edges of the crotch portion which delimit the leg openings advantageously have a curved contour.

The inventive method:

The method according to the features of the independent method claim for producing an incontinence article in the form of pants for receiving body excretions is also in accordance with the invention, which comprises a front belly portion and a rear back portion which are connected to each other at side seam areas on both sides at the manufacturer's for forming a belly and back band that is continuous in the transverse and peripheral hip direction with a hip opening that is closed in the peripheral hip direction, and with a crotch portion which comprises an absorbent body and extends in a longitudinal direction between the belly portion, with a transverse edge facing the crotch, and the back portion, with a transverse edge facing the crotch, wherein the crotch portion is undetachably joined to the belly portion and the back portion, wherein the inventive method comprises providing the crotch portion, and providing the crotch portion comprises the following method steps:

supplying an endless cover sheet material web that forms the subsequent cover sheet material, applying a reinforcing means onto areas of the cover sheet material web as a reinforcing coating in such a fashion that the reinforcing means is disposed on the subsequent inner side of the cover sheet material such that the reinforcing means is provided in each case in an area that bridges the respective subsequent longitudinal edge of the absorbent body, i.e. covers a respective subsequent longitudinal edge area of the absorbent body and is also provided at least in a respectively bordering subregion of the subsequent projection such that the reinforcing means in this subregion, as viewed in the transverse direction, is smaller than the projection, supplying a backsheet material web that forms the subsequent backsheet material, supplying and arranging absorbent bodies at a separation from each other between the cover sheet material web and the backsheet material web.

Mounting the crotch portion to the belly portion and/or to the back portion can be optimized by introducing a reinforcing means to the respective area bridging the subsequent longitudinal edge of the absorbent body. In this fashion, the natural stability of the absorbent body is transferred to the bordering subregion of the projection of materials with small surface densities by means of the introduced reinforcing means. The reinforcing means in the subregion of the projection improves the technical manageability of the otherwise unstable projection. This permits accurate and flat depositing of the projection.

In accordance with a preferred embodiment of the inventive method, the reinforcing means is applied in such a fashion that only the projection in the rear overlapping area comprises a reinforcing means.

In accordance with a further preferred embodiment of the inventive method, the reinforcing means is applied in such a fashion that the projection comprises reinforcing means both in the rear overlapping area and in the front overlapping area.

In a further preferential embodiment, the reinforcing means is applied in such a fashion that the reinforcing means extends starting from the front and/or rear overlapping area over the respective transverse edge, facing the crotch, of the belly portion and/or back portion towards the transverse center axis.

In a further particularly preferred embodiment, the reinforcing means is applied in such a fashion that the reinforcing means in the front overlapping area and the reinforcing means in the rear overlapping area extend towards the transverse center axis in such a fashion that they are joined.

In accordance with a preferred embodiment of the inventive method, the reinforcing means is applied in such a fashion that the reinforcing means covers the subregion of the subsequent projection with a width G' relative to the respective projection (66a, 66b) with a width H in the transverse direction with a ratio G'/H of at least 0.10, in particular at least 0.15, moreover, in particular, at least 0.20 and at most 0.80, in particular at most 0.75, moreover, in particular at most 0.70.

In accordance with a further preferred embodiment of the inventive method, the reinforcing means is applied in such a fashion that the reinforcing means covers the respective longitudinal edge area with a width G" relative to the width H of the projection in the transverse direction with a ratio G"/H of at least 0.10, in particular at least 0.15, moreover in particular at least 0.20, but advantageously at most 0.80, in particular at most 0.75, moreover, in particular, at most 0.70.

In accordance with a further preferred embodiment of the inventive method, the reinforcing means is applied in such a fashion that the reinforcing means of the subsequent longitudinal edge area covers the absorbent body in the transverse direction in total, i.e. on both sides, with a ratio of at least 5%, in particular, at least 10%, moreover, in particular, at least 15% and at most 35%, in particular, at most 30% and moreover, in particular at most 25% relative to the width (K) of the absorbent body.

In accordance with a further preferred embodiment of the inventive method, the reinforcing means is applied in such a fashion that the reinforcing means covers the subsequent respective longitudinal edge area of the absorbent body with a width G" relative to the width (K) of the absorbent body with a ratio G"/K of at least 0.02, in particular at least 0.04, moreover, in particular at least 0.06, but advantageously at most 0.30, in particular, at most 0.25 and moreover, in particular, at most 0.20.

It is particularly advantageous for the reinforcing means to be applied with an overall width G of 10 to 60 mm, in particular 15 to 55 mm, moreover in particular 20 to 50 mm, moreover, in particular, 20 to 40 mm.

The reinforcing means is preferentially applied in such a fashion that the subregion covered by the reinforcing means in the transverse direction of the respective projection has a width G' of more than 5 mm, preferably more than 10 mm, but preferably less than 50 mm, moreover advantageously less than 40 mm, moreover advantageously less than 30 mm.

It is particularly advantageous for the reinforcing means to be applied in such a fashion that the longitudinal edge area of the absorbent body covered by the reinforcing means in the transverse direction has a width G" of more than 5 mm, preferably more than 10 mm, but preferably less than 50 mm moreover less than 40 mm, moreover less than 30 mm.

In accordance with a further advantageous embodiment, the reinforcing means is applied parallel to the subsequent longitudinal direction and in the form of strips having a constant width.

In this fashion, the reinforcing means can be directly introduced into the incontinence article in the machine direction and thereby also quicker and at reduced cost with little technical expense.

The reinforcing means is also advantageously applied as a reinforcing coating with a surface density of 1 to 30 $g/m^2$, in particular of 2 to 20 $g/m^2$, moreover, in particular 2 to 10 $g/m^2$. The surface densities of this coating maintain the flexible properties of the non-woven cover sheet material having a surface weight of 5 to 20 $g/m^2$. With regard to manufacture, excessive coating surface densities would disadvantageously additionally result in that the coating means penetrates through the per se thin cover sheet material to the other upper side of the cover sheet material which can cause disadvantageous soiling of the machines through uncontrolled coating inputs e.g. onto cylinders and rollers, which is particularly disadvantageous when coating means in the form of adhesive are used.

In a further advantageous embodiment, the reinforcing coating is applied in the form of an adhesive, in particular, of a hot melt adhesive, moreover, in particular, of a hydrophobic hot melt adhesive.

In one particularly preferred embodiment, the reinforcing coating is applied in the form of a fully coated strip, in particular in a contact-free method. Contact-free coating methods are known. The technology is described in the documents EP 0 901 781 B1 and EP 1 459 719 A2.

In a further preferred embodiment of the inventive method, separate joining means are provided, preferably in a limited region, in the area of the projection between the cover sheet material and the backsheet material and/or between the cover sheet material and the absorbent body and/or between the backsheet material and the absorbent body. More preferably, in accordance with the method, the backsheet material and the cover sheet material are directly connected in the area of the projection by separate joining means such as adhesive, calender welding or ultrasonic welding, in particular, up to the longitudinal edge of the crotch portion. More preferably, in accordance with the method, such separate joining means are advantageously also provided between the backsheet material and the absorbent body and/or between the cover sheet material and the absorbent body. These joining means are advantageously not provided throughout the entire surface but in the form of a discontinuous pattern. The use of adhesive is advantageously also suited to reinforce the adhesive action of the joining means which connect the backsheet material and/or the cover sheet material and/or the absorbent body. In as far as an adhesive is provided for these separate joining means, the adhesive may e.g. be disposed in the form of strips, in the form of a grid or a spiral pattern.

The cover sheet material web is also advantageously introduced into the method step in the form of a composite of a liquid-permeable topsheet material web that forms the subsequent topsheet material, with longitudinal edges and bordering longitudinal edge areas, and of hydrophobic barrier means material webs forming the subsequent barrier means, which are joined in seams on both sides on the longitudinal edges or longitudinal edge areas of the topsheet material web.

It is thereby particularly advantageous for this composite to apply the reinforcing means in such a fashion that the reinforcing means covers the joints of the cover sheet material web.

It is basically feasible to prefabricate the crotch portions of the incontinence article as described above and then supply them in an endless fashion to the further process, i.e. like from a roll. It is, however, also advantageous to form the crotch portions within a continuous method.

The inventive method for producing the incontinence article in the form of pants thereby advantageously comprises the following methods steps:

- supplying two partial webs on the basis of a non-woven material that form the subsequent belly portion or the subsequent back portion of the incontinence article,
- supplying and applying the second elastification means to the two partial webs and fixing them thereto,
- combining the crotch portions and the two partial webs in such a fashion that one end of the crotch portions is arranged in a longitudinal direction transversely to the machine direction to be level with one partial web and the other end to be level with the other partial web in the front and/or rear overlapping area, and the crotch portions are disposed at a separation from each other in the machine direction, and fixing the crotch portions and the partial webs in the overlapping areas and further transport in the machine direction,
- supplying, applying and fixing the first elastification means in the machine direction to the partial webs,
- folding about a folding line that extends in the machine direction in such a fashion that one partial web comes to rest on top of the other partial web,
- joining the superimposed partial webs transversely to the machine direction at separations from each other for forming side seam areas of the incontinence articles to be produced, and obtaining products comprising a belly portion, a back portion and an intermediate crotch portion,
- carrying out a separating cut transversely to the machine direction and obtaining finished and singled incontinence articles.

In a further preferred embodiment of the inventive method, the second elastification means are supplied in such a fashion that they extend, starting from the two side seam areas (14), in the direction (56) towards a longitudinal center axis (44) of the incontinence article (2) and thereby fan out in a curved fashion with increasing separation from each other.

Leg elastification means are moreover advantageously supplied between the covering materials of the crotch portion, i.e. between the cover sheet material web and the backsheet material web.

The leg elastification means are moreover advantageously supplied in such a fashion that they follow the contour of the absorbent body.

The leg elastification means are moreover advantageously supplied in such a fashion that they extend at a varying separation from the absorbent body and have a greater separation from the absorbent body at their longitudinal ends than at the center.

The leg elastification means are moreover advantageously supplied in the form of an arc. In a particularly advantageous fashion, the leg elastification means are supplied such that the leg elastification means substantially follow the curved leg cut-outs of the subsequent crotch portion.

In a further advantageous embodiment, the crotch portions have leg cut-outs formed by a first contour cut for forming substantially curved leg cut-outs.

In a preferred embodiment of the method, the first contour cut is performed in such a fashion that substantially curved leg cut-outs of the subsequent crotch portions of the incontinence article are formed.

In one particularly preferred embodiment, the first contour cut is performed using a cutting roller pair, i.e. a rotational knife with an anvil roller.

The inventive method including introduction of reinforcing means has turned out to be particularly advantageous precisely for the production of incontinence articles, in which the large projection of chassis-forming covering materials of the crotch portion with a small surface density is subjected to a first contour cut.

The introduction of reinforcing means is moreover advantageous for crotch portions having leg elastification means that are associated with the leg openings. When in this case the respective crotch portions are provided with leg elastification means and are then separated, the leg elastification means exert high tensile forces on the materials of the respective crotch portion and tend to gather the crotch portion. This is difficult to control in terms of production technology, and it is even more difficult for separated crotch portions to provide the leg openings with a contour. However, the part of the leg openings that is delimited by the crotch portion is already produced during performance of the first contour cut at a time at which the crotch portions are not yet separated, i.e. are still endlessly supplied. With this endless supply, the above-explained forces that are generated by the leg elastification means can be better controlled such that in consequence thereof, the accuracy of the leg opening contour can be improved with reduced technical difficulty.

It is basically feasible for the cover sheet material web, backsheet material web and absorbent body to be supplied in the subsequent longitudinal direction of the crotch portion of the hygiene article. Supply in the transverse direction is also feasible. In the first case, a deflection through 90° is required in the course of the endless production method, since further production is advantageously performed in the transverse direction of the incontinence articles. In any case, the crotch portions must be separated, i.e. singled transversely to the machine direction and then be further transported at a separation from each other in order to be connected to the endless partial webs that form the subsequent belly portion and the subsequent back portion.

The backsheet material web is preferably supplied in the form of a liquid-impermeable material as described above.

The absorbent body advantageously comprises materials that absorb body fluids, as described above.

The leg elastification means that are used are made from the preferred materials and have the preferred pretensions as described above.

For supplying the two partial webs that form the subsequent belly portion and the subsequent back portion of the incontinence article, it is e.g. feasible to unroll each partial sheet from its own roll and supply it to the production method. In accordance with a preferred method variant, it is also possible to initially supply an endless non-woven material web which is then separated along the machine direction to form the two partial webs. In this fashion, the machine must be equipped with only one roll.

The non-woven partial webs of the subsequent belly portion and/or the subsequent back portion are preferably made from the above-described materials having the above-described surface densities.

The first and/or second elastification means are advantageously supplied in an endless fashion to the partial webs in the machine direction. With particular preference, the first and second elastification means are endlessly supplied to the partial webs in the machine direction.

The above-mentioned first elastification means that extend in the peripheral hip direction are advantageously introduced at a separation of 4 to 10 mm, in particular 4 to 8 mm, in particular 4 to 6 mm from each other.

The second elastification means that fan out in a curved fashion in the direction towards the longitudinal center axis of the incontinence article, are correspondingly introduced at a varying separation from one another (separation of directly bordering elastification means) of between 3 mm and 35 mm. The elastification means are advantageously introduced by guiding instruments for the elastification means, which can be driven in an oscillating fashion.

The second elastification means are advantageously introduced in such a fashion that a minimum separation between the second elastification means (i.e. the separation between directly neighboring second elastification means) in the subsequent side seam areas is 3 to 8 mm, in particular 3 to 7 mm and moreover, in particular 3 to 6 mm.

The second elastification means are moreover advantageously introduced in such a fashion that a maximum separation between the second elastification means (i.e. the separation between directly neighboring elastification means) on a subsequent absorbent body edge or a subsequent longitudinal edge of the crotch portion is 7 to 35 mm, in particular 10 to 32 mm and moreover, in particular, 12 to 30 mm.

The second elastification means are advantageously introduced in such a fashion that the separations between the second elastification means in the subsequent back portion differ from the separations between the second elastification means in the subsequent belly portion. The second elastification means are advantageously introduced in such a fashion that the maximum separation of the second elastification means from each other in the subsequent back portion is larger than the maximum separation between the second elastification means in the subsequent belly portion.

The second elastification means are moreover advantageously introduced in such a fashion that they have a fanning-out degree F of $$F=(A-B)/B*100\%$$

as described above.

The shape of the second elastification means and the design of the second contour cut of the partial webs are advantageously such that the second contour cut is performed along and at a separation (D) from each innermost second elastification means in the longitudinal direction facing the crotch. This separation (D) is advantageously 2 to 40 mm, in particular 3 to 30 mm, and moreover, in particular, 4 to 20 mm.

The first and/or the second elastification means that are pretensioned as described above are fixed to the partial sheets. The pretension is thereby defined as a factor of the stretch rate compared to the unstretched/relaxed state of the elastification means.

Advantageous materials and thicknesses as described above are used for the first and/or second elastification means.

The first and/or second elastification means is/are advantageously fixed to the partial webs using adhesive. The adhesive for fixing the first and/or the second elastification means may thereby be advantageously directly applied to the partial webs and/or non-woven covering sheets or be directly applied to the elastification means (thread glueing). The first elastification means are advantageously directly provided with adhesive, in particular sprayed, and the second elastification means are disposed onto an adhesive that was previously extensively applied to the partial webs and/or non-woven covering layers.

In a further advantageous embodiment, a second contour cut that cuts the partial webs at their mutually facing edge portions is performed for forming substantially curved cut-out sections for the legs prior to folding about a folding line that extends in the machine direction.

In accordance with another preferred embodiment of the inventive method, the second contour cut only cuts the partial webs but not the crotch portion. For this reason, it is possible to form a discontinuous shape along the leg openings in the transition area between the crotch portion and the belly portion or the back portion.

In accordance with a preferred embodiment of the inventive method, the second contour cut of the partial webs is performed in such a fashion that the curved cut-out section for the legs of the partial web of the subsequent belly portion has a different shape, in particular, a different angle or radius than the curved cut-out section for the legs of the partial web of the subsequent back portion.

In accordance with a preferred embodiment, the second contour cut for forming the substantially curved cut-out sections for the legs is performed in such a fashion that the second contour cut of the partial web of the subsequent belly portion and of the partial web of the subsequent back portion are performed simultaneously.

In one particularly preferred embodiment, the second contour cut is performed using a cutting roller pair, i.e. a rotational knife with an anvil roller.

It may also be advantageous when joining of the superimposed partial webs for forming side seam areas of the incontinence articles to be produced and performance of the separating cut are realized in the same method step.

BRIEF DESCRIPTION OF THE DRAWING

Further features, details and advantages of the invention can be extracted from the enclosed claims and the drawing and the following description of a preferred embodiment of the inventive incontinence article. In the drawing:

DESCRIPTION OF THE PREFERRED EMBODIMENT

Figure 1:
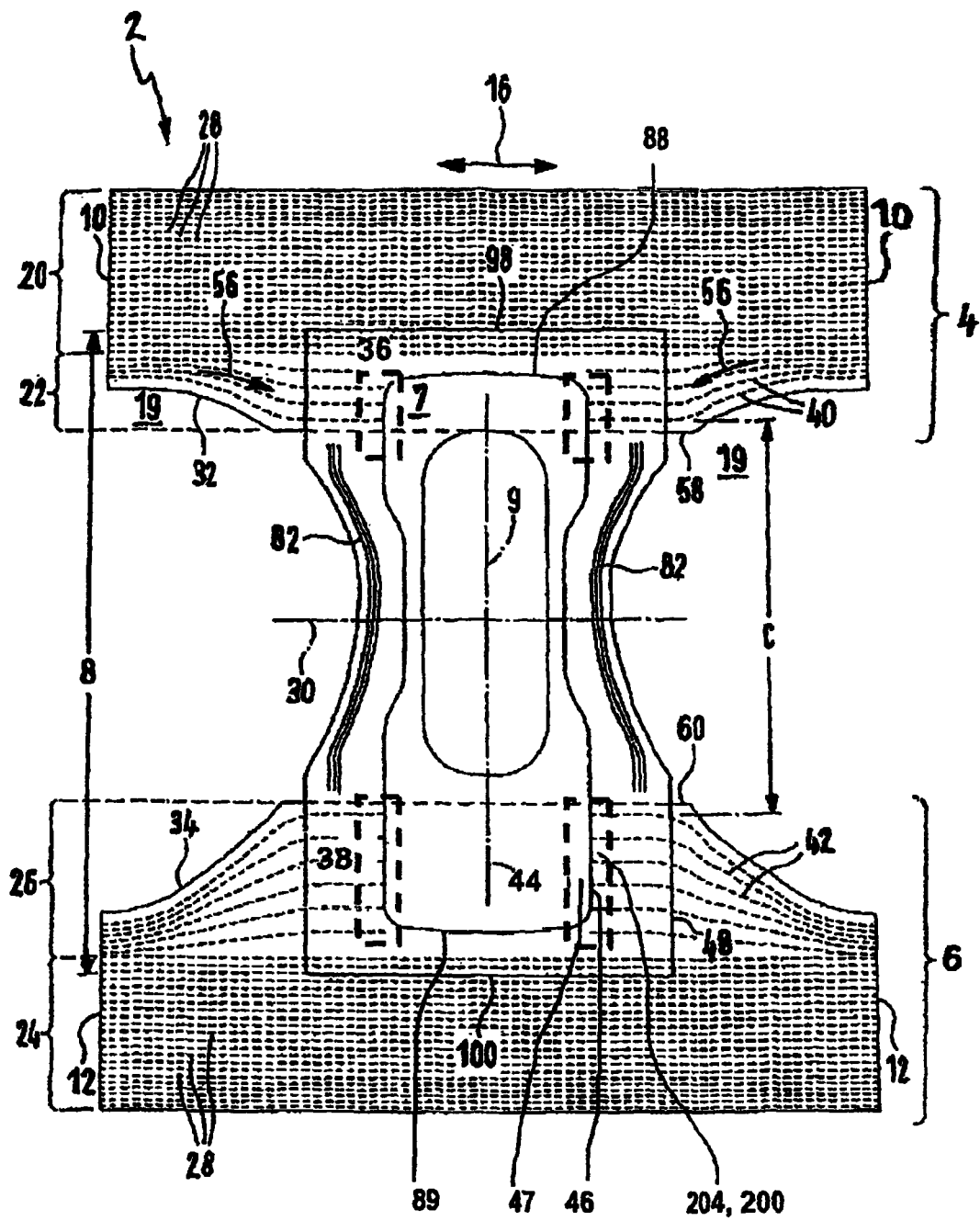
FIG. 1 shows a top view of an inventive incontinence article, wherein a belly portion, a back portion and a crotch portion connecting the belly and the back portion of the incontinence article are not yet connected to form a pants shape, but are shown in a flat and extended state.
Figure 6:
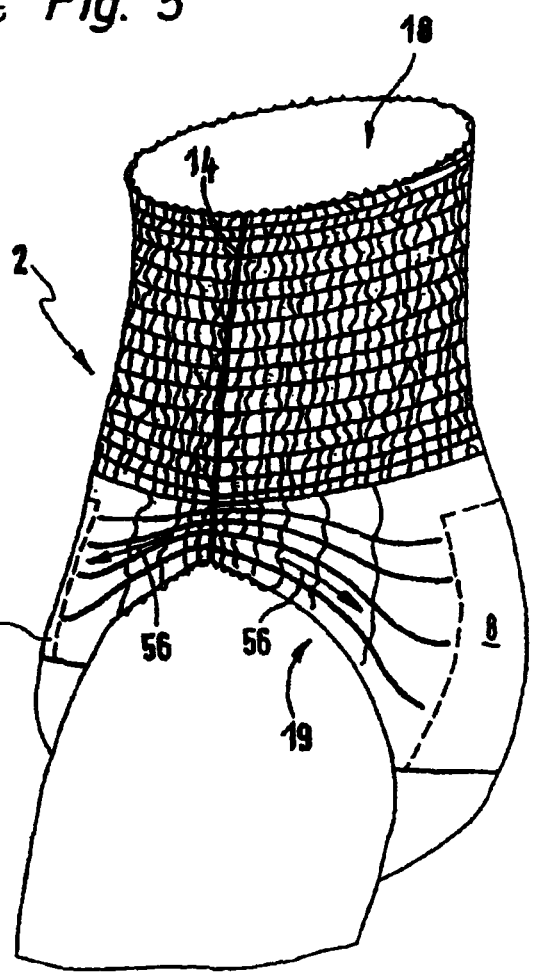
FIG. 6 shows a perspective view (schematic) of the incontinence article that is applied to a user in accordance with FIG. 1.

The figures show an incontinence article in the form of pants designated in total with reference numeral 2 for receiving solid and liquid body excretions. The incontinence article 2 is formed from three components which can be largely produced independently of each other, i.e. a front belly portion 4, a rear back portion 6, and an interposed crotch portion 8 comprising an absorbent body 7, wherein a substantial surface portion of the crotch portion 8 overlaps the belly portion 4 and also overlaps the back portion 6 and is undetachably connected thereto in the overlapping area at the manufacturer's. This produces an H-shaped basic structure of the incontinence article with a longitudinal direction 9 as illustrated in FIG. 1. The joined components shown in FIG. 1 are then connected to each other also at the manufacturer's for forming the pants shape (schematically illustrated in FIG. 6) at the respective lateral longitudinal edge sections 10, 12 of the belly portion 4 and the back portion 6, thereby forming side seam areas 14 (FIG. 6) on both sides. In the pants-shaped state of the incontinence article as finished by the manufacturer's, the belly portion 4 and the back portion 6 extend in the transverse or peripheral hip direction 16 in a continuous fashion to the side seam areas 14, and thereby define a hip opening 18 that is closed in the peripheral hip direction, and leg openings 19 through which the user puts on the incontinence article like pants.

The belly portion 4 can be divided into an area 20 on the hip side and an area 22 on the crotch side facing the leg openings. A corresponding subdivision is provided in the back portion i.e. also in an area 24 on the hip side and an area 26 on the crotch side facing the leg openings.

First elastification means 28 are provided in the area 20 on the hip side of the belly portion 4 and in the hip-sided area 24 of the back portion 6, which elastification means may e.g. be, in particular, thread-shaped elastification means such as Lycra® threads, which are connected in a pre-stretched state, in the so-called stretch bond method to the flat materials (chassis materials) of the belly portion 4 and the back portion 6. These first elastification means 28 extend in the transverse or peripheral hip direction 16 from a side seam area 14 to the other.

The portion 22 of the belly portion 4 or 26 of the back portion 6 on the crotch side facing the leg openings 19 have an edge contour 32 or 34 that is different from the transverse or peripheral hip direction 16 and extends towards a transverse center axis 30 of the crotch portion 8. In the illustration of FIG. 1, this edge contour 32, 34 is also curved and is therefore suited to delimit the leg openings 19. This shape of the area 22 or 26 on the crotch side facing the leg openings also realizes a relatively large overlapping area 36, 38 between the crotch portion 8 and the belly portion 4 or back portion 6, which is essential in view of a tear proof connection between the crotch portion 8 and the belly portion 4 or the back portion 6. The larger the overlapping area 36, 38, the smaller the required amounts of adhesive in relation to the surface of the overlapping area, which is advantageous in view of the stiffness of the chassis materials. In particular, the components may be connected in that the adhesive is not applied to the overall surface.

Figure 7:
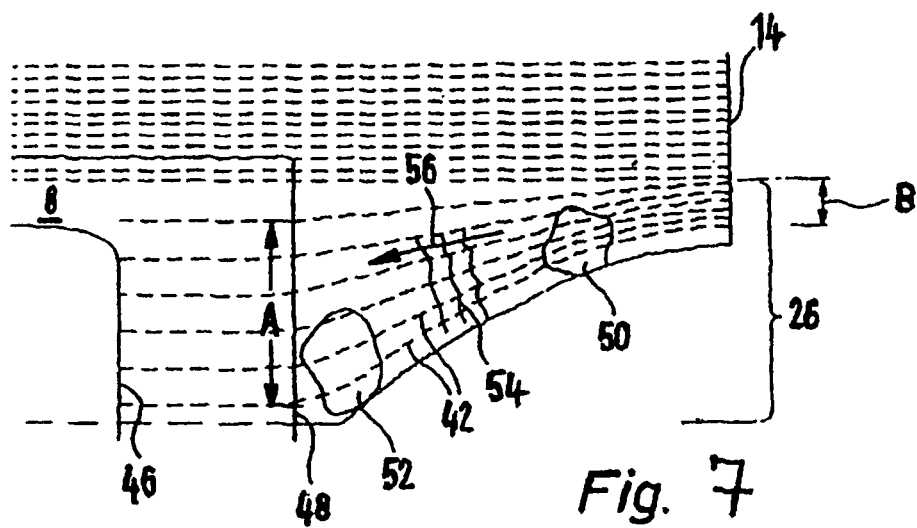
FIG. 7 shows sections of the incontinence article of FIG. 1.
Figure 8:
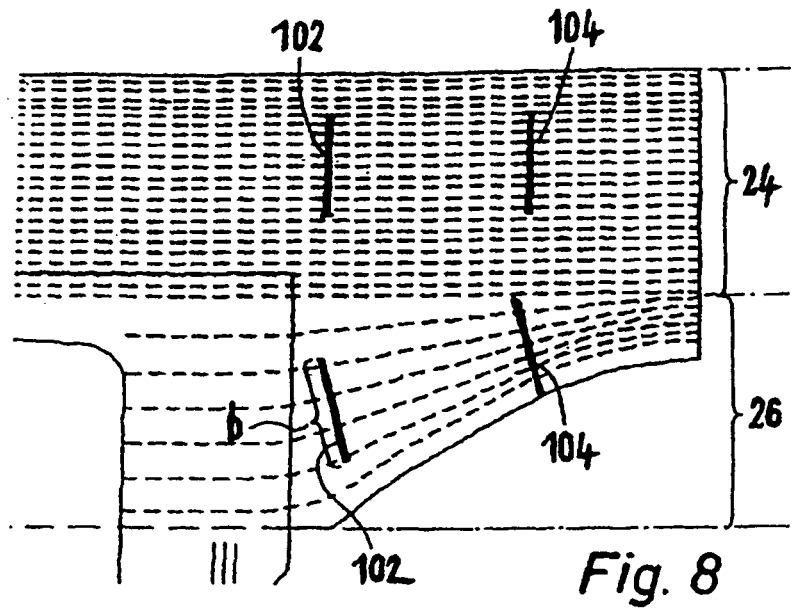
FIGS. 8 and 9 illustrate by way of example the determination of restoring forces in the belly portion or back portion of the incontinence article.
Figure 9:
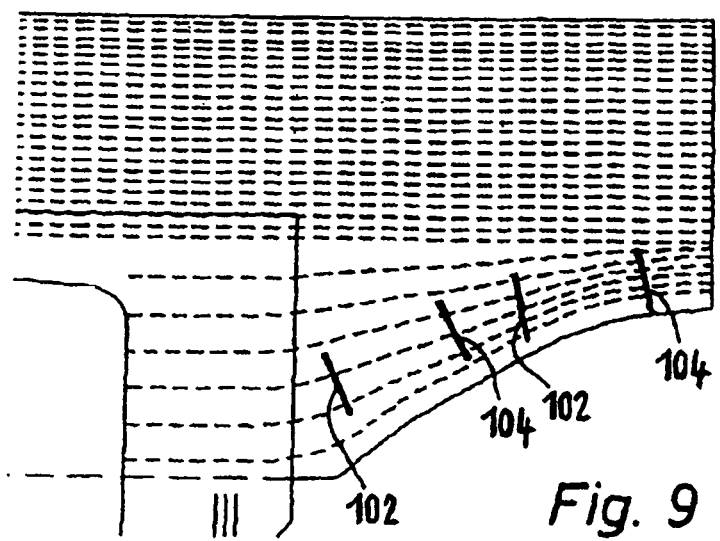

The respective area 22, 26 of the belly portion 4 or the back portion 6 on the crotch side facing the leg openings 19 is also elasticised. Second elastification means 40 or 42 are provided at that location. The second elastification means 40, 42 each extend from the side seam areas 14 towards a longitudinal center axis 44 of the incontinence article. As can be gathered from FIGS. 1 and 7, the second elastification means 40, 42 fan out in the direction towards the longitudinal center axis 44. This means that the separation between them increases towards the longitudinal center axis 44. This fanning out of the second elastification means 40 or 42 can also be designated in more detail with respect to quantity by means of FIG. 7. The second elastification means 42 of the back portion 6 illustrated in FIG. 7 have e.g. a minimum separation of 3 to 8 mm from each other in the side seam areas 14 (separation between directly neighboring elastification means) and a maximum separation (separation between directly neighboring elastification means) of 7 to 35 mm from each other on an absorbent body edge 46 or a longitudinal edge 48 of the crotch portion 8. With respect to FIG. 7 the fanning-out degree F can also be defined as follows:

$$F=(A-B)/B*100\%$$

This fanning-out degree may advantageously be between 50 and 900%, in particular, between 100 and 700% and moreover, in particular, between 150 and 550%. It is advantageously larger in the back portion 6 than in the belly portion 4. The values A and B are thereby defined as the separation between the outermost second elastification means 40, 42 in the longitudinal direction 9 and the innermost second elastification means 40, 42 in the longitudinal direction 9 (i.e. not the separation between directly neighboring elastification means): i.e. A as the maximum separation, in particular, at the longitudinal edge 48 of the crotch portion 8 and B as the minimum separation, in particular, in the side seam area 14 (cf. FIG. 7).

When the fanning-out degree of the second elastification means 40, 42 is selected to be sufficiently large, a decreasing restoring force can be realized within the area 22 or 26 on the crotch side facing the leg openings 19 in the direction 56 towards the crotch portion 8 provided that the pretension is not excessively increased as a consequence of the arc shape of the second elastification means 40, 42 facing away from the hip or transverse direction 16 due to the larger distance of these second elastification means 40, 42. Considering a region 50 of the relevant area 22 or 26 on the crotch side that is closer to the side seam area 14 in comparison with a region 52 closer to the crotch portion 8, the restoring force that is generated by extensive stretching of the region 52 (stretching in the direction of the elastification means 42) is smaller than the restoring force that is generated when the region 50 is stretched. In consequence thereof, the chassis materials of the belly portion 4 and of the back portion 6 are advantageously less gathered due to the smaller elastic forces that are exerted by the second elastification means 40, 42 in the illustrated case, such that the number of folds/frills 54 is also reduced, i.e. starting from the respective side seam area 14 in the direction towards the crotch portion 8. Since the restoring forces generated by extensive stretching of the belly portion in the area 22 of the belly portion 4 or 26 of the back portion 6 on the crotch side facing the leg openings decrease in the direction of the arrow 56, i.e. generally from the side seam area 14 towards the crotch portion 8, the wear comfort is considerably improved, since it was found out that the elastically stretchable materials are particularly problematic in exactly these areas, since the materials are substantially subjected to tensile and expansive stress in these areas corresponding to the physiognomy of the human body shape. A previously not realized degree of freedom is thereby created by deliberately advantageously reducing this restoring force, i.e. decreasing the restoring force in the direction of the arrow 56, i.e. in the direction approaching the crotch portion 8.

In the illustrated preferred embodiment of the incontinence article 2, a separation C between the innermost second elastification means 40, facing the crotch, of the belly portion 4 and the corresponding innermost second elastification means 42, facing the crotch, of the back portion 6 is between 250 and 420 mm, depending on the size of the incontinence article. The second elastification means 40, 42 substantially extend to the transverse edge 58, 60, facing the crotch, of the belly portion 4 and the back portion 6. The separation between the belly portion 4 and the back portion 6 is 250 to 400 mm.

The separation between the innermost second elastification means 40, 42 facing the crotch and the edge contour 32, 34, defining the leg openings, of the area 22, 26 on the crotch side facing the leg openings, of the belly portion 4 and the back portion 6 is advantageously 2 to 40 mm, moreover advantageously 3 to 30 mm, in particular 4 to 15 mm.

The extension of the belly portion 4 and of the back portion 6 in the side seam area 14 in the longitudinal direction 9 is advantageously between 100 and 220 mm. The extension of the crotch portion 8 in the transverse direction 16 is advantageously 200 to 350 mm.

Figure 3:
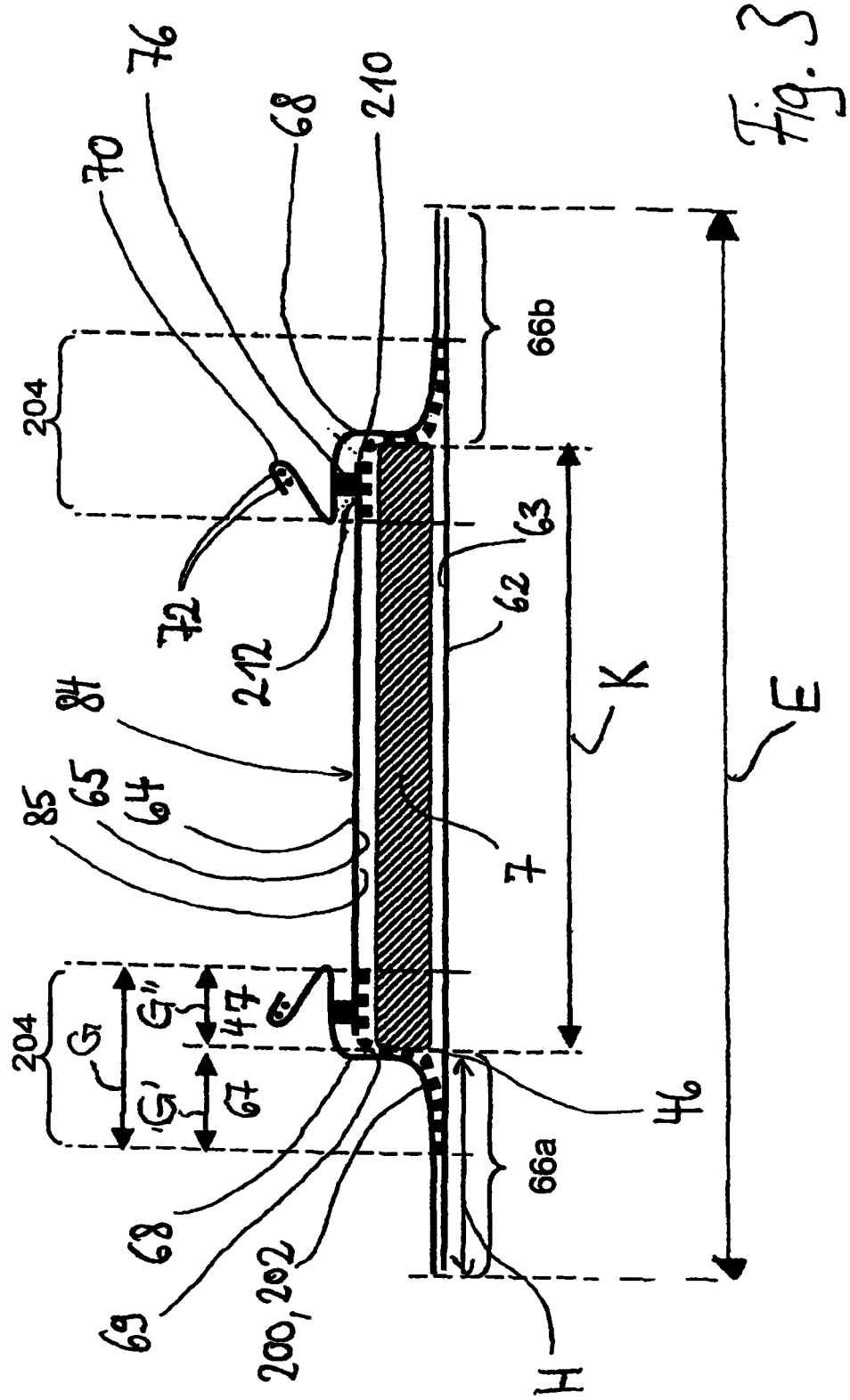
FIG. 3 shows a sectional view (schematic) along a transverse center axis of the crotch portion with cutting plane III-III in FIG. 2*b*.
Figure 4:
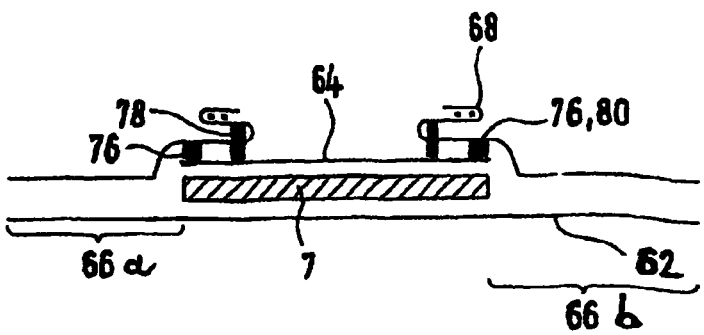
FIG. 4 shows a sectional view (schematic) of the crotch portion with cutting plane IV-IV in FIG. 2*b*.
Figure 5:
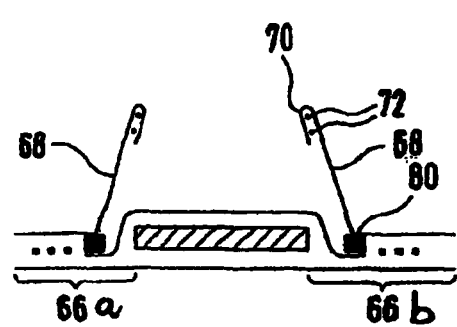
FIG. 5 shows a sectional view (schematic) of the crotch portion with cutting plane V-V in FIG. 2*b*.

The crotch portion 8 comprises a liquid-impermeable backsheet material 62 that may be formed, in particular, by a breathable but liquid-tight foil material, and a cover sheet material 84 which is preferably produced on the basis of a non-woven material and is a composite of a topsheet material 64 formed on the basis of a non-woven material and barrier means 68 provided on both sides. The absorbent body 7 is disposed between the backsheet material and the topsheet material as illustrated in FIGS. 3, 4, 5. The absorbent body 7 has longitudinal edges 46 and bordering longitudinal edge areas 47. In the exemplary case, the backsheet material 62 forms a projection 66a, 66b on each side of the longitudinal edges 46 in the transverse direction 16. The topsheet 64 only slightly projects past the absorbent body 7 in the transverse direction. However, one upright barrier means 68 is provided on each side of the absorbent body 7, which extends in the longitudinal direction 9 and is typically called an upright cuff element or collar element, and is preferably formed from a hydrophobic, in particular, liquid-impermeable non-woven material, which preferably extends in the transverse direction 16 to the lateral longitudinal edges 48 of the crotch portion 8. The barrier means 68 is thereby joined at joints 76 to the longitudinal edges 210 or the longitudinal edge areas 212 of the topsheet material 64. The distal ends 70 of the barrier means 68 are provided with further elastification means 72, which lift the barrier means 68 against the skin surface of the user during use of the incontinence article, as is schematically shown in FIG. 5. In their respective longitudinal end areas 74, the lateral barrier means 68 are fixed, via schematically indicated fixations 78, to the topsheet 64 or to themselves in a C-shaped folded configuration in addition to being fixed in the joints 76. It is thereby advantageous and notable that each inner fixation 78 in FIG. 4 fixes the barrier means 68 onto itself in the transverse direction 16 within the outer fixation 76, which forms a cuff base line 80 that continuously extends in the longitudinal direction 9. However, the inner fixation 78 is only provided in the longitudinal end areas 74 of the barrier means 68.

It is thereby particularly advantageous for the extension of the above-mentioned projection 66a, 66b of the backsheet material 62 and/or the cover sheet material 84 along both sides of the longitudinal edges 46 of the absorbent body 7 added together to be at least 25% with respect to the largest width E of the crotch portion 8. This provides space in the transverse direction 16 for the arrangement of leg elastification means 82 that extend along the leg openings 19. It has turned out to be advantageous for the leg elastification means 82 to extend at a given separation from the absorbent body 7 which comprises a great deal of material and is therefore rather rigid in order not to exert any additional extension or torsional forces onto the absorbent body, which could impair its absorption properties, and also to realize a liquid-tight leg termination which is largely independent of the absorbent body. In the present case, it has turned out to be particularly advantageous for the leg elastification means 82 to terminate in the longitudinal direction 9 at a clear distance of, in particular, at least 10 mm, preferably at least 20 mm, upstream of the second elastification means 40 and 42 of the belly portion 4 or the back portion 6. These leg elastification means 82 preferably terminate in the longitudinal direction 9 upstream of the belly portion 4 and the back portion 6. This is advantageous and essential since, in this case, the leg elastification means 82 do not or hardly influence the stress behavior of the belly portion 4 and the back portion 6. It was found out that, in view of the advantageous aim of improving wear comfort, in particular, in the areas 22 and 26 of the belly portion 4 and of the back portion 6 on the crotch side facing the leg openings 19, it is disadvantageous for the leg elastification means 82, which usually have a great pretension and correspondingly large restoring force, to additionally also extend at that location.

As is illustrated in FIG. 1, the crotch portion 8 projects to a relatively large extent 66a, 66b past the longitudinal edges 46 of the absorbent body 7 in the transverse direction 16, in particular, also in areas of the crotch portion 8, which face the belly portion 4 or the back portion 6. As mentioned above, this yields a relatively large overlapping area 36, 38 between the crotch portion 8 and the belly portion 4 and the back portion 6. According to a preferred embodiment variant, the overlapping area 36 of the crotch portion 8 and the belly portion 4 covers at least 12% of the surface of the belly portion 4, and the overlapping area 38 of the crotch portion 8 and of the back portion 6 covers at least 20% of the surface of the back portion 6. This is advantageous, since the crotch portion 8 is thereby reliably fixed to the belly portion 4 or the back portion 6 even when the adhesive is not provided on the overall surface. It is thereby also advantageously sufficient to use adhesive only in sections or in a pattern in order to realize a connection. This advantageously prevents the joined materials from becoming excessively rigid.

As is shown in FIG. 1, the incontinence article 2 comprises reinforcing means 200 which are disposed in the front and rear overlapping area 36, 38. In combination with FIG. 3, which illustrates a schematic sectional view along the plane III-III of FIG. 2b, it becomes clear that the reinforcing means 200 is thereby disposed in an area 204 that bridges the respective longitudinal edge 46 of the absorbent body 7. The reinforcing means 200 thereby covers the respective longitudinal edge area 47 of the absorbent body 7 and also a subregion 67 of the projection 66a, 66b bordering the longitudinal edge 46.

The backsheet material 62 and the cover sheet material 84 are connected in the area of the projection 66a, 66b by a separate joining means (not illustrated in FIG. 3). A separate joining means is also provided between the backsheet material and the absorbent body and between the cover sheet material and the absorbent body. These separate joining means are applied in the form of an adhesive, not over the entire surface, but in the form of a discontinuous pattern. These separate joining means in the form of an adhesive are thus e.g. applied in the form of a grid, strips or a spiral pattern.

The reinforcing means 200 is disposed on the inner side 85 of the cover sheet material 84. The cover sheet material is, like in the present example, a composite of a topsheet 64 and barrier means 68 joined to both sides of the longitudinal edges 210 or longitudinal edge areas 212 of the topsheet 64. The reinforcing means 200 is thereby applied in such a fashion that the joint 76 connecting these two materials is covered. The reinforcing means 200 is thereby applied in the form of a reinforcing coating 202, in the form of an adhesive, in particular of a hot melt adhesive. A hydrophobic adhesive is thereby particularly preferred, in particular, the adhesive LC 3001ZP by the company Fuller (H.B. Fuller Deutschland GmbH, An der Roten Bleiche 2-3, 21335 Lüneburg, Germany). The reinforcing coating 202 is thereby applied with a surface density of 2 to 10 g/m$^2$.

The reinforcing means 200 in the bridging area 204 has an overall width G of 20 to 50 mm, in particular, advantageously 20 to 40 mm. In the subregion 67 of the projection 66a, 66b covered by the reinforcing means 200, the reinforcing means has a width G' of advantageously more than 5 mm and less than 30 mm. The reinforcing means 200 covers the respective subregion 67 of the projection (66a, 66b) in the transverse direction in such a fashion that the ratio G'/H between the subregion (67), covered by the reinforcing means (200), of the respective projection (66a, 66b) having the width (G') and the respective projection (66a, 66b) with the width (H) is at least 0.10 but advantageously at most 0.8.

The reinforcing means 200 advantageously covers the longitudinal edge area 47 of the absorbent body 7 in the transverse direction with a width G" of advantageously more than 5 mm and less than 30 mm. The reinforcing means 200 covers the longitudinal edge area 47 of the absorbent body 7 in such a fashion that the ratio G"/H between the respective longitudinal edge area 47, covered by the reinforcing means 200, with a width G" and the respective projection 66a, 66b with the width (H) is at least 0.10 but advantageously at most 0.80. The reinforcing means 200 covers the longitudinal edge area 47 of the absorbent body 7 in total, i.e. on both sides, with a fraction of at least 10% and at most 35% relative to the width K of the absorbent body 7.

In the preferred embodiment as indicated in FIG. 1, both the front overlapping area 36 and the rear overlapping area 38 have reinforcing means 200.

The reinforcing means 200 in the front and rear overlapping areas 36, 38 differ with respect to their extension in the longitudinal direction 9. The reinforcing means 200 in the front and rear overlapping areas 36, 38 thereby each extend at least to the transverse edge 88, 89 of the absorbent body 7, to the transverse edge 58, facing the crotch, of the belly portion 4, and to the transverse edge 60, facing the crotch, of the back portion 6.

Figure 2:
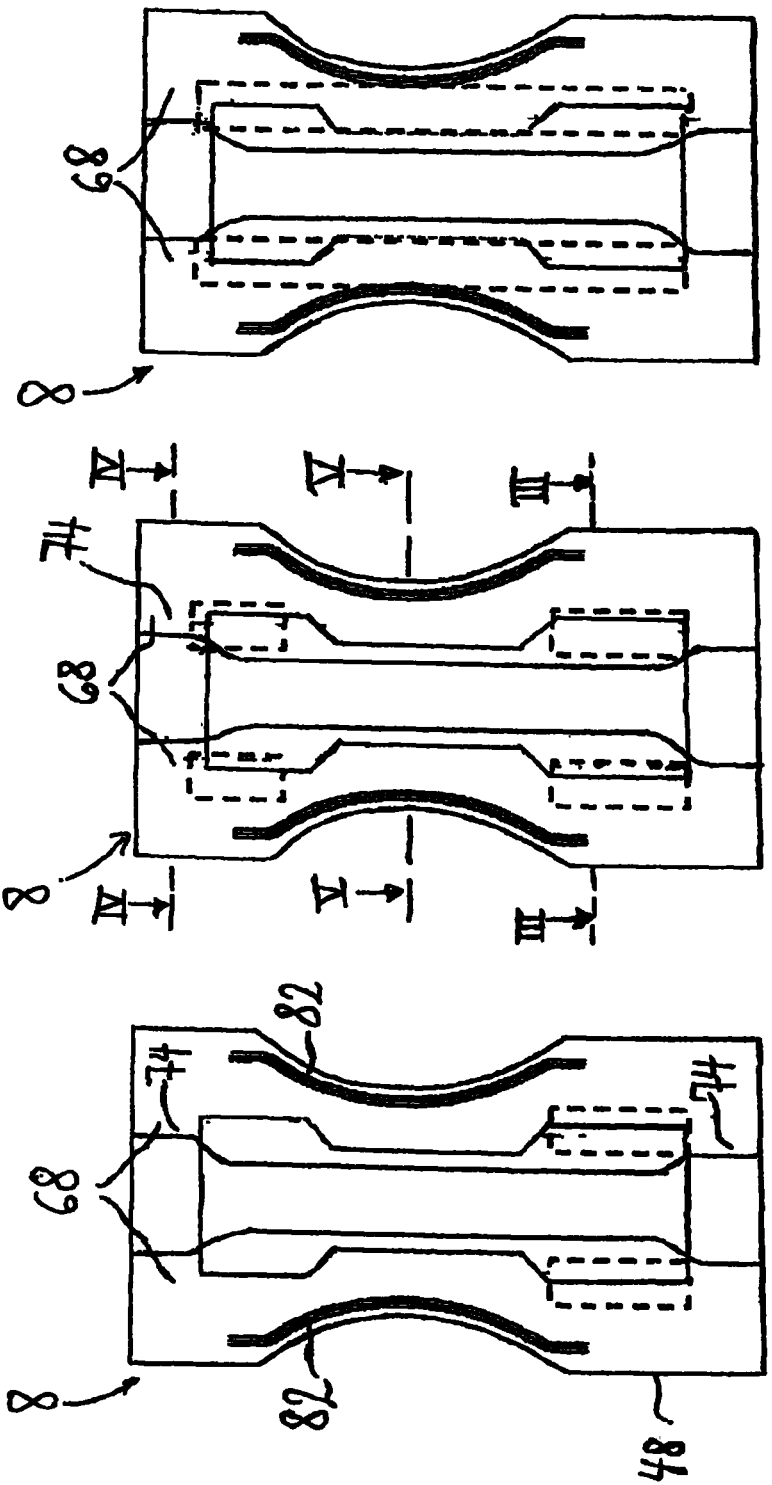
FIGS. 2*a*, 2*b*, 2*c* show top views of advantageous embodiments of the crotch portion of the incontinence article according to FIG. 1 again in a flat and extended state.

Further embodiments of the reinforcing means are also feasible. FIGS. 2a, 2b, 2c show top views of a crotch portion 8 of the incontinence article according to FIG. 1 in the flat and expanded state. The crotch portion 8 (FIG. 1) including the reinforcing means 200 integrated in the front and rear overlapping areas 36, 38 (schematically illustrated in FIG. 2b) can be replaced by an alternative embodiment of the crotch portion 8 (schematically illustrated in FIGS. 2a and 2c).

FIG. 2a shows a crotch portion 8 of the incontinence article according to FIG. 1 in the flat and expanded state with reinforcing means 200 which, in the schematic view, are then only provided in the rear overlapping area 38 of the overall incontinence article 2.

FIG. 2c shows a crotch portion 8 of the incontinence article 2 according to FIG. 1 in the flat and expanded state with reinforcing means 200 which, in the schematic view, are then provided in the front and rear overlapping areas 36, 38 of the overall incontinence article 2. Starting from the front and the rear overlapping areas 36, 38, the reinforcing means 200 extend via the respective transverse edge 58, 60, facing the crotch, of the belly portion 4 and of the back portion 6 in the direction towards the transverse center axis 30 in such a fashion that the reinforcing means 200 extend in the direction towards the transverse center axis 30 and are thereby connected to each other.

Figure 10:
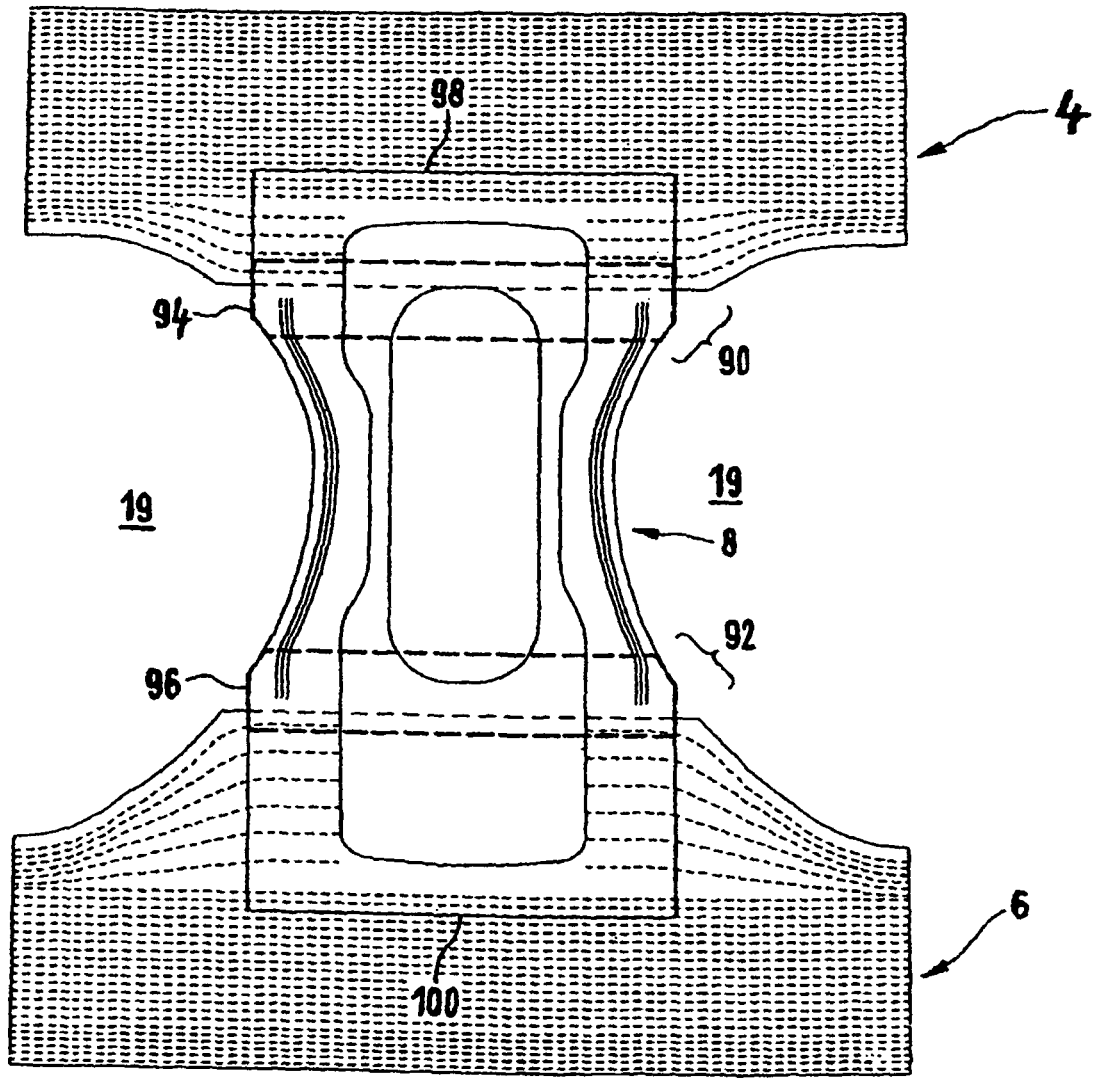
FIG. 10 shows a top view corresponding to FIG. 1 of the inventive incontinence article for clearly illustrating the connection between the crotch portion and the belly portion or back portion.

FIG. 10, which corresponds to FIG. 1, explains a further advantageous detail of a preferred embodiment of the incontinence article. The three-component concept for producing the inventive incontinence article produces a transition 90 between the crotch portion 8 and the belly portion 4, as well as a transition 92 between the crotch portion 8 and the back portion 6, which usually yields a non-continuous shape, i.e. with corners, angles or bends, of the edges of the chassis materials, which define the leg openings 19. This is dangerous in that force peaks are formed in the area of the transitions 90, 92, which could tear the chassis materials, which could, in turn, impair joining of the crotch portion 8 to the belly portion 4 or to the back portion 6. To counteract this, the respective transition 90 and 92 is provided with a reinforcing coating 94, 96 of the liquid-impermeable backsheet material 62 of the crotch portion 8. It is sufficient to provide this reinforcing coating 94, 96 only in the area indicated by the dashed line of FIG. 10. In the exemplary, advantageously illustrated case, the reinforcing coating 94, 96 overlaps the belly portion 4 and the back portion 6 in the longitudinal direction 9 by only approximately 10 to 20 mm, in particular, by approximately 15 mm. The reinforcing coating terminates in the longitudinal direction 9 in each case upstream of the longitudinal ends 98, 100 of the crotch portion, at least 30 mm upstream of the belly-side longitudinal end 98 and at least 90 mm upstream of the back-side longitudinal end 100. This is advantageous in that the reinforcing coating 94, 96 does not thereby unnecessarily reinforce the chassis materials in areas where this is not helpful but rather undesired and disadvantageous. This also saves material costs. However, the possibility to provide the reinforcing coating 94, 96 not only in the transition 90 or 92 remains unaffected.

The reinforcing coating 94, 96 advantageously consists of a non-woven material, in particular of a spunbonded non-woven material of polypropylene, in particular, having a surface density of 10 to 20 g/m$^2$, in particular 12 to 17 g/m$^2$.

Figure 11:
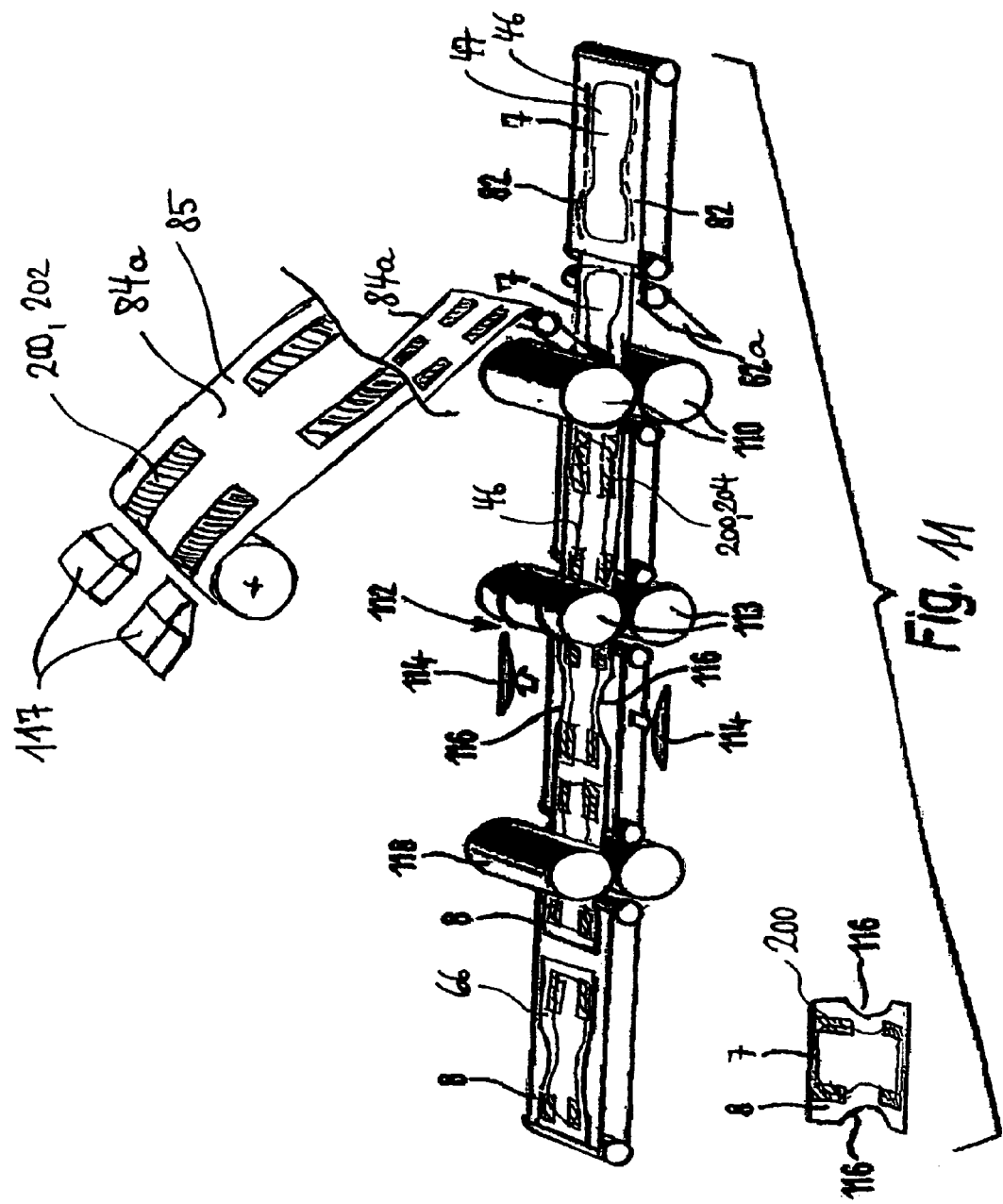
FIG. 11 shows a schematic view of the inventive method for producing the crotch portion.
Figure 12:
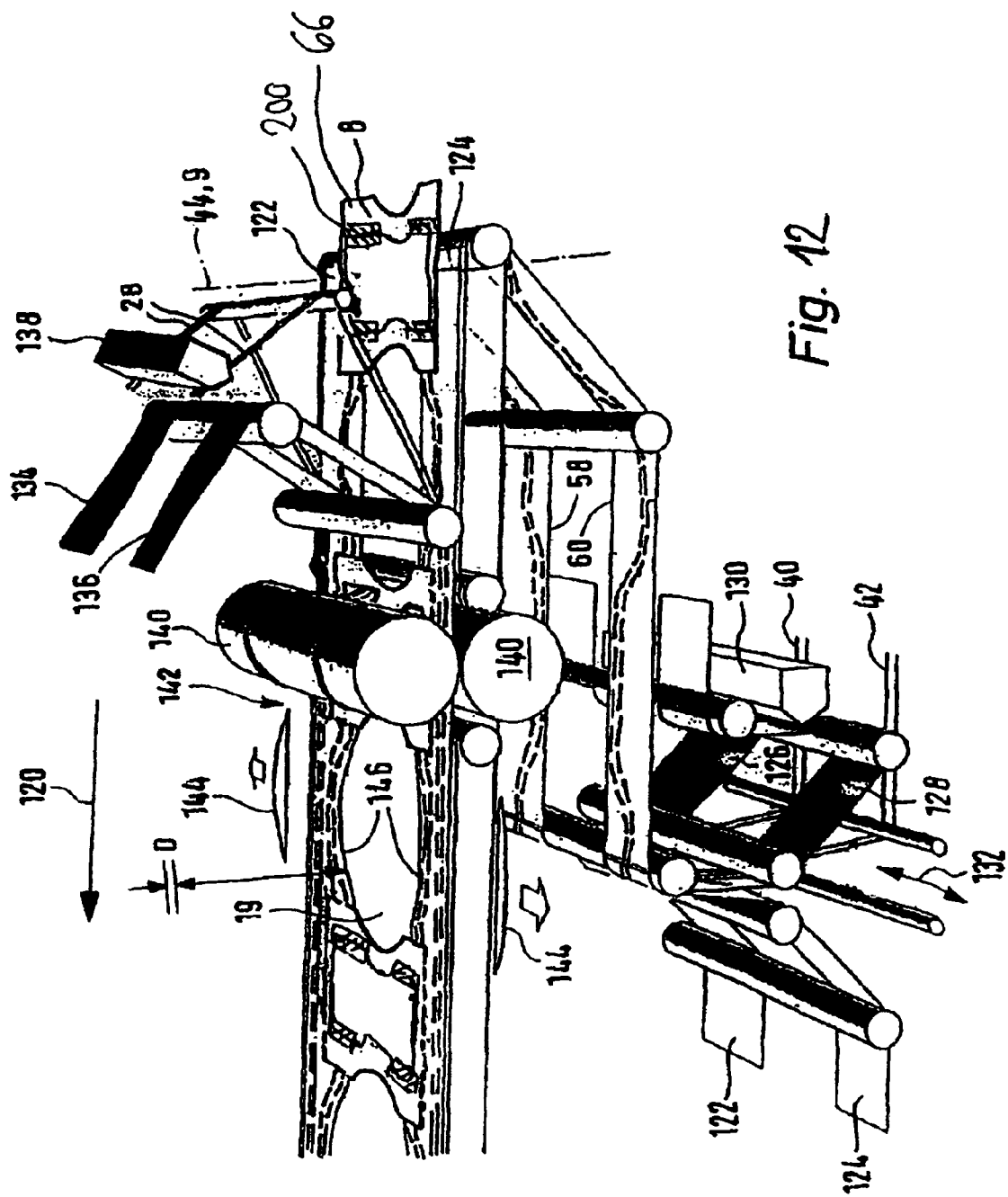
FIG. 12 shows a schematic view of supplying and joining partial sections to the crotch portion and performance of a second contour cut.
Figure 13:
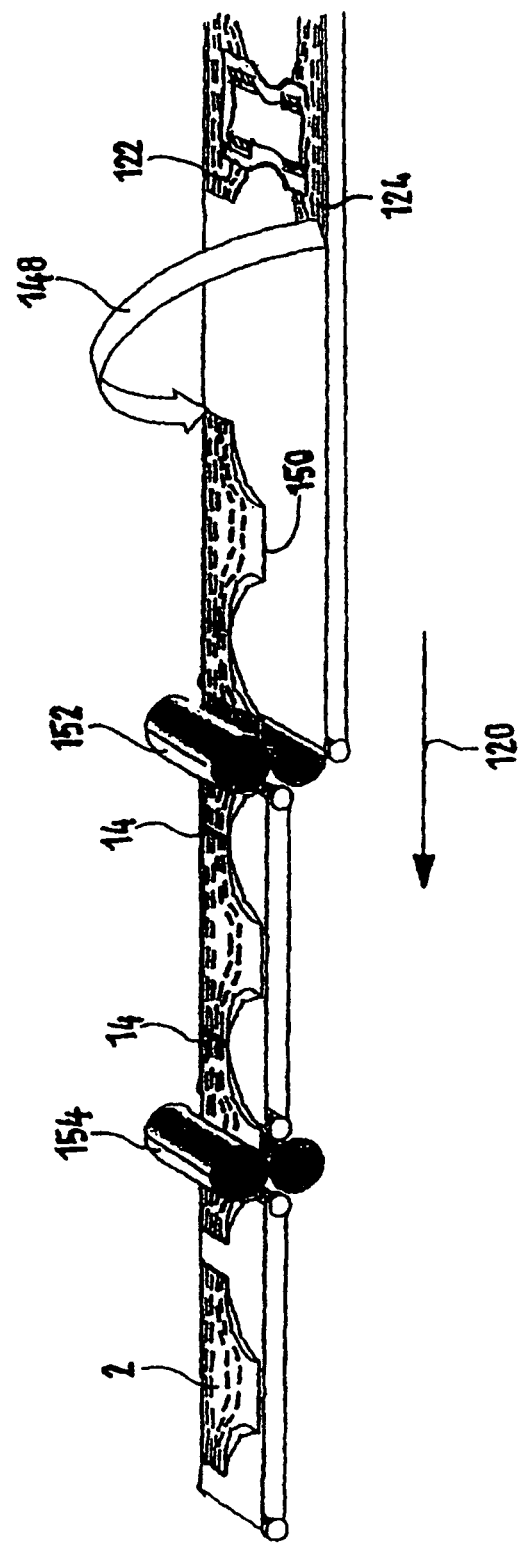
FIG. 13 shows a schematic view of folding into a pants shape and forming side seam areas, and subsequent separation of the hygiene articles.

Inventive method:

FIGS. 11 through 13 show the inventive production method. Towards this end, an endless backsheet material web 62a and an endless cover sheet material web 84a, and, in succession, the absorbent body 7 and (only indicated) the leg elastification means 82 that are associated with the subsequent leg openings, are supplied to a fast running production machine.

A reinforcing means 200 in the form of a reinforcing coating 202 is previously applied to the subsequent inner side 85 of the endless cover sheet material web 84a, wherein the coating material is provided from schematically shown nozzles 117. The reinforcing coating 202 is advantageously applied onto the cover sheet material web 84a using a contact-free coating method. The reinforcing coating is advantageously provided on the overall surface.

The reinforcing means 200 is thereby applied in such a fashion that the reinforcing means 200 is disposed in one area 204 in each case bridging the longitudinal edge 46 of the absorbent body 7 after joining the cover sheet material web 84a and the absorbent body 7. The reinforcing means 200 thereby extends over both the longitudinal edge area 47 of the absorbent body 7 bordering the longitudinal edge 46 and a bordering subregion 67 of the projection 66.

The absorbent bodies 7 are disposed at a separation from each other between the cover sheet material web 84a and the backsheet material web 62a, and the composite that is thereby formed is fixed through suitable separate joining means, in particular adhesive, which is preferably not applied over the entire surface but e.g. in the form of a grid, lines or in the form of a spiral pattern. The leg elastification means 82 are also supplied and fixed between the cover sheet material web 84a and the backsheet material web 62a. This is realized by a first roller pair 110 and an adhesive in a fashion that is not illustrated. For completeness, it should be mentioned that the crotch portion 8 additionally comprises lateral upright and preferably elasticised cuffs as side leakage protection. In the present case, these are already provided on the side of the cover sheet material web 84a facing the body but are not shown. They may also be introduced at any point of the production process (FIG. 11) or at a later point.

Downstream of the above-described processes, the composite is subjected to a first contour cut 112 using a cutting roller pair 113. The contour cut 112 includes cutting curved segments 114 out of the composite of backsheet material web 62a and cover sheet material web 84a forming the crotch portion 8 to thereby form the cut-outs 116 for the legs in the crotch portion 8. The composite is then supplied to a downstream cutting station 118 where a separating cut is performed transversely to the supply direction for singling the crotch portions 8 of the incontinence article to be produced. FIG. 11 also indicates a perspective view of the crotch portion 8 with absorbent body 7, reinforcing means 200 and leg cut-outs 116.

After separation of the crotch portions 8, the crotch portions are turned through 90° during continued supply, and are then further supplied in the machine direction 120 transversely to the subsequent longitudinal center axis 44 of the incontinence article 2 (FIG. 12). As is also shown in FIG. 12, partial webs 122, 124 on the basis of non-woven material are supplied for producing the subsequent belly portion 4 and back portion 6 of the incontinence article. These partial webs 122, 124 may be formed starting from one single web through separation in the longitudinal direction. The above-mentioned second elastification means 40 and 42 are disposed onto these partial webs 122, 124, and are thereby also supplied in an endless fashion and in the supply direction of the partial webs 122, 124. For fixing the second elastification means 40, 42 to the partial webs 122, 124, a non-woven cover layer 126, 128, which was previously loaded with glue in a glue application station 130, is applied in each case such that the second elastification means 40, 42 are laminated between the partial webs 122, 124 and the non-woven cover layers 126, 128. FIG. 12 is a schematic view and therefore does not explicitly show that the second elastification means 40, 42 are supplied at a varying separation from each other, which is realized by an oscillating guiding means (indicated by the double arrow 132). The curved fanning-out shape of the second elastification means 40, 42 in the direction towards the crotch portion 8 is thereby formed through corresponding control of the guiding means for each individual elastification means 40, 42.

The partial webs 122, 124 are then further supplied in the above-mentioned composite and joined with the crotch portions 8 such that one end of the crotch portions overlaps the partial web 122 in a longitudinal direction 9 transversely to the machine direction 120 and the other end thereof overlaps the other partial web 124.

The reinforcing means 200 stabilizes the projection 66 of the crotch portion 8. The subregion of the projection covered by the reinforcing means can thereby advantageously be arranged on the partial webs 122, 124, i.e. the subsequent belly portion and back portion without forming folds. The crotch portions 8 are thereby arranged with respect to the partial webs 122 and 124 in such a fashion that the reinforcing means 200 is at least provided in the area overlapping the partial webs 122, 124.

The crotch portions 8 are supplied in such a fashion that, after being joined, they are disposed at a separation from each other in the machine direction 120. The crotch portions 8 and the partial webs 122, 124 are fixed to each other in the configuration of FIG. 11, and are further transported in the machine direction 120.

The first elastification means 28 that extend in the transverse or peripheral hip direction 16 are then supplied in an endless fashion in the machine direction 120 and fixed to the partial webs 122, 124. Non-woven material webs 134, 136 are again supplied. However, the adhesive is not directly applied onto the non-woven material webs 134, 136 but is disposed onto the first elastification means 28. The first elastification means 28 are then disposed on the partial webs 122, 124 and covered by the non-woven material webs 134, 136 such that they are laminated.

It is also feasible to provide each individual elastification means 28, 40, 42 with adhesive, i.e. to glue each thread. It is also feasible to omit the elastification means 28, 40, 42 and the non-woven cover layers 126, 128, 134 and/or 136 irrespective of the way in which the adhesive is applied. However, the non-woven cover layers are advantageous in that they simultaneously form a soft inner side of the incontinence article.

Subsequent thereto, FIG. 12 shows a further cutting roller pair 140, i.e. a rotating knife with an anvil roller, between which the previously formed composite is guided through in the machine direction 120 with the described orientation. A second contour cut 142 is thereby performed, in the course of which one respective curved segment 144 is advantageously separated from each partial web 122, 124, i.e. from the mutually facing transverse edges or edge sections 58 and 60 of the partial webs 122, 124, to also form leg cut-outs 146 for the partial webs 122, 124. Since the second contour cut 142 does not include the crotch portion 8 but only the partial webs 122, 124, the second contour cut 142 extends substantially along the machine direction 120 at a small angle transversely thereto. In this fashion, the cut can be optimally configured like the first contour cut 112 during production of the crotch portion 8. On the whole, the subsequent leg openings 19 of the incontinence article 2 can be formed with high precision in accordance with the requirements that are regarded as optimal. The second contour cut 142 on the partial web 122 may thereby advantageously have a different shape than on the partial web 124. The shape of the leg cut-outs 146 or the subsequent leg openings 19 of the incontinence article 2 may thereby have different configurations in the belly portion 4 and in the back portion 6.

The composite formed in this fashion is further transported and folded onto itself in a folding station 148 (only indicated in FIG. 13) about a folding line 150 that extends in the machine direction 120, such that one partial web 124 comes to rest on top of the other partial web 122. Subsequent thereto, a respective side seam area 14 is formed between the partial webs 122, 124 in a joining station 152, i.e. the actual pant shape is formed. Subsequent to this method step, a separating cut is performed transversely to the machine direction 120 in a separating station 154, as a result of which the finished incontinence articles 2 are singled. It is also feasible to design the joining station 152 at the same time as a separating station, e.g. in the form of a cut welding means, such that the side seam areas 14 are formed and the incontinence articles 2 are singled at the same time.

Figure 14:
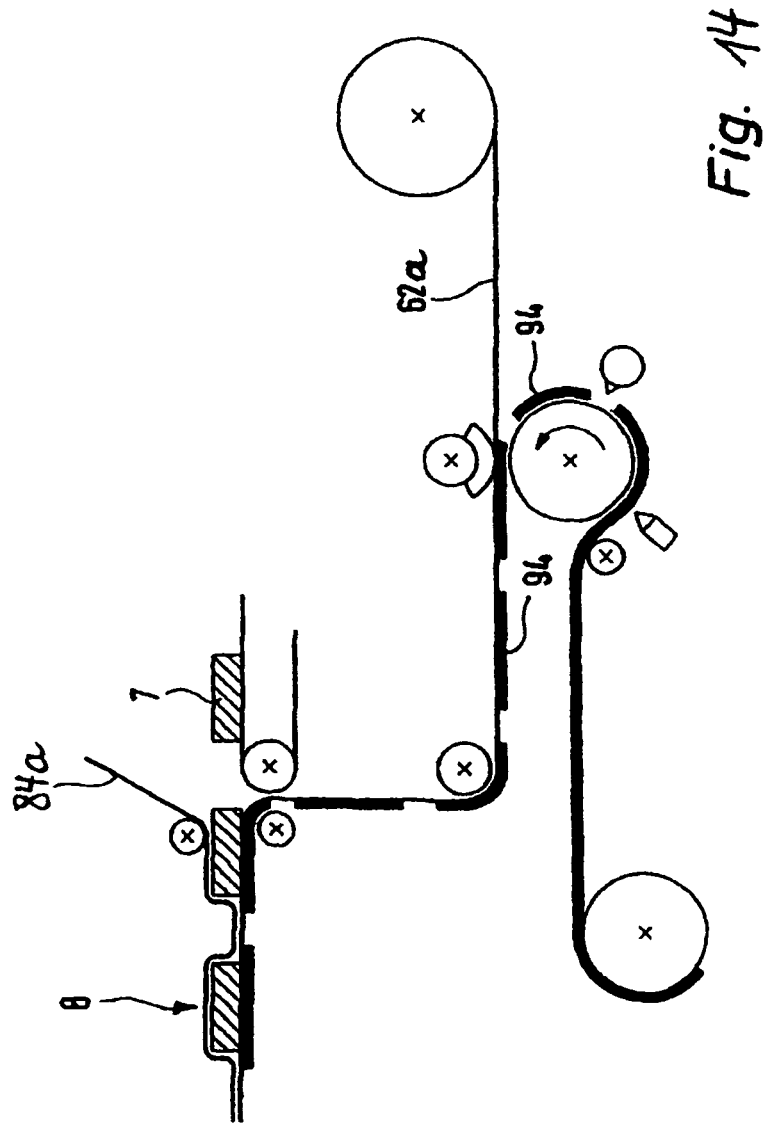
FIG. 14 shows a schematic view, in which some areas a backsheet material are coated during the production of the crotch portion of the hygiene article.

FIG. 14 finally schematically shows a process, in which sections of the backsheet material web 62a are provided with a reinforcing coating 94 described in connection with FIG. 10, i.e. during supply of the backsheet material web 62a for producing the crotch portions, which was already explained in connection with FIG. 10. In contrast to FIG. 10, the reinforcing coating 94, which may, in particular, be a non-woven material section, extends substantially over a major part of the crotch portion 8. The backsheet material web 62a at the longitudinal ends of the crotch portion 8 to be formed remains uncoated.

We claim:

1. An incontinence article in the form of pants for receiving body excretions, the article comprising:
    a front belly portion;
    a rear back portion;
    side seam areas generated by a manufacturer and connecting together said belly portion and said back portion on both sides of the article to form a belly and back band which is continuous in a transverse or peripheral hip direction, thereby defining a hip opening which is closed in said peripheral hip direction;
    a crotch portion extending in a longitudinal direction between said belly portion, at a transverse edge thereof facing a crotch, and said back portion, at a transverse edge thereof facing the crotch, wherein said crotch portion is permanently attached to said belly portion and said back portion, said crotch portion, said belly portion and said back portion thereby defining leg openings of the incontinence article;
    first elastification elements disposed in said belly portion and said back portion, said first elastification elements extending at a separation from and parallel to each other in said peripheral hip direction to thereby extensively elasticise said belly portion and said back portion;
    second elastification elements disposed in an area of said belly portion and said back portion on a crotch side facing said leg openings;
    a liquid-impermeable backsheet material disposed in said crotch portion, said backsheet material having an inner side and a surface density of 10 to 40 g/m$^2$;
    a cover sheet material on a basis of a non-woven material, said cover sheet material having an inner side and a surface density of 5 to 20 g/m$^2$;
    an absorbent body disposed in said crotch portion between said backsheet material and said cover sheet material, said absorbent body having a width, longitudinal edges, bordering longitudinal edge areas and transverse edges;
    a projection, said projection formed by said cover sheet material or by said cover sheet material and said backsheet material, said projection extending past respective said longitudinal edges of said absorbent body in a transverse direction, wherein said crotch portion has a width of at least 200 mm in said transverse direction and said projection has a total size at both sides of said longitudinal edges of said absorbent body of at least 25% with respect to a maximum width of said crotch portion, wherein said crotch portion overlaps at least 12% of a surface of said belly portion in a front overlapping area, and at least 20% of a surface of said back portion in a rear overlapping area; and
    a reinforcing means disposed on said inner side of said cover sheet material in said projection at said front and/or said rear overlapping area in areas bridging a respective said longitudinal edge of said absorbent body to cover said longitudinal edge area, said reinforcing means being disposed in at least each bordering subregion of said projection, wherein, as viewed in said transverse direction, said reinforcing means in said subregion is smaller than said projection, said reinforcing means comprising or consisting essentially of a reinforcing coating having a surface density of 1 to 30 g/m$^2$.

2. The incontinence article of claim 1, wherein, in both said front and said rear overlapping areas, said reinforcing means is disposed in an area that bridges said respective longitudinal edge of said absorbent body.

3. The incontinence article of claim 1, wherein said reinforcing means extend in a longitudinal direction at least to said transverse edge of said absorbent body and to said transverse edge, facing the crotch, of said belly portion and/or of said back portion.

4. The incontinence article of claim 1, wherein said reinforcing means extend towards a transverse center axis from said front and/or rear overlapping areas past respective said transverse edge, facing the crotch, of said belly portion and/or of said back portion.

5. The incontinence article of claim 1, wherein said reinforcing means in said front overlapping area and said reinforcing means in said rear overlapping area extend towards a transverse center axis, thereby being connected to each other.

6. The incontinence article of claim 1, wherein a ratio G'/H between said subregion, covered by said reinforcing means, of a respective said projection having a width G' and a respective said projection having a width H is at least 0.10 but not more than 0.80.

7. The incontinence article of claim 1, wherein a ratio G"/H between a respective said longitudinal edge area covered by said reinforcing means having a width G" and a respective said projection having a width H is at least 0.10 but not more than 0.80.

8. The incontinence article of claim 1, wherein said reinforcing means covers said longitudinal edge area of said absorbent body in said transverse direction in total on both sides, with a fraction of at least 5% but not more than 35% with respect to said width of said absorbent body.

9. The incontinence article of claim 1, wherein said reinforcing means has an overall width of 10 to 60 mm.

10. The incontinence article of claim 1, wherein said reinforcing means is disposed parallel to said longitudinal direction in a form of a strip of constant width.

11. The incontinence article of claim 1, wherein said reinforcing coating has a surface density of 2 to 20 g/m$^2$.

12. The incontinence article of claim 1, wherein said reinforcing coating comprises an adhesive, a hot melt adhesive or a hydrophobic hot melt adhesive.

13. The incontinence article of claim 1, wherein said cover sheet material is a composite of a liquid-permeable topsheet material with longitudinal edges and bordering longitudinal edge areas and hydrophobic barrier means joined at seams on both sides of the longitudinal edge areas of topsheet material.

14. The incontinence article of claim 13, wherein said reinforcing means covers said seams of said cover sheet material.

15. The incontinence article of claim 1, wherein said projection of said backsheet material and/or of said cover sheet material in said transverse direction, is in total on both sides of said longitudinal edges of said absorbent body, 25 to 50%, 30 to 45% or 35 to 45% of a maximum width of said crotch portion.

16. The incontinence article of claim 1, wherein said second elastification means extend starting from said two side seam areas in a direction towards a longitudinal center axis of the incontinence article and thereby extend in a curve and fan out with increasing separation from each other.

* * * * *